(12) United States Patent
Prendergast et al.

(10) Patent No.: US 7,705,022 B2
(45) Date of Patent: Apr. 27, 2010

(54) IDO INHIBITORS AND METHODS OF USE THEREOF

(75) Inventors: George C. Prendergast, Penn Valley, PA (US); William P. Malachowski, Collegeville, PA (US); Alexander J. Muller, Media, PA (US); James B. DuHadaway, Wilmington, DE (US)

(73) Assignee: Lankenau Institute for Medical Research, Wynnewood, PA (US)

( * ) Notice: Subject to any disclaimer, the term of this patent is extended or adjusted under 35 U.S.C. 154(b) by 573 days.

(21) Appl. No.: 11/589,024

(22) Filed: Oct. 27, 2006

(65) Prior Publication Data

US 2007/0105907 A1    May 10, 2007

Related U.S. Application Data

(60) Provisional application No. 60/730,706, filed on Oct. 27, 2005.

(51) Int. Cl.
- *A61K 31/4439* (2006.01)
- *A61K 31/381* (2006.01)
- *A61K 31/4045* (2006.01)
- *C07D 333/58* (2006.01)
- *C07D 401/12* (2006.01)
- *C07D 209/14* (2006.01)

(52) U.S. Cl. .............. 514/339; 514/415; 514/443; 546/277.4; 548/503; 548/506; 548/507; 549/58

(58) Field of Classification Search ............. 514/339, 514/415, 443; 546/277.4; 548/503, 507, 548/506; 549/58
See application file for complete search history.

(56) References Cited

FOREIGN PATENT DOCUMENTS

| SU | 507 567 | 3/1976 |
|---|---|---|
| WO | 2004/093871 | 2/2004 |
| WO | 2007/050963 | 5/2007 |

OTHER PUBLICATIONS

R. Andreasch Monatshefte fuer Chemie 1918, 39, 419-40 (CAS abstract and structure attached).*

Muller et al. Cancer Res. 2005 65 (18), 8065-68.*
Boasso et al. Current Drug Metabolism 2007, 8, 217-23.*
Cancer Reference Information, www.cancer.org Jan. 11, 2009.*
V.T. Zsolnai (Arzneimittel-Forschung 1968, 18(10), 1319-1324.*
Mohanta, P.K., et al., "1-(Methyldithiocarbonyl: a Useful Thiocarbonyl Transfer Reagent for Synthesis of Substituted Thioureas." Tetrahederon, 56(4): 629-637 (Jan. 1, 2000).
Orth, R.E., et al. "Preparation of Some 1-Substituted 1,2,3,4-Tetrazole-5-thiones." Journal of Pharmaceutical Sciences, 51:862-864 (1962).
Fisyuk, A.S., et al. "Interaction of Methyl N-(3-Oxoalkyl)Carbamates, S-Methyl -Carbamates, and -Dithiocarbamates with Sodium Borohydride. Synthesis of Tetrahydro-1,3-Oxazin-2-Ones and -Thiones." Chemistry of Heterocyclic Compounds, 37(5): 597-609 (2001).
Fisyuk, A.S., et al. "Synthesis of 6-hydroxytetrahydro-1,3-thiazine-2-thiones and methyl esters of 3-oxoalkyldithiocarbamic acids from 1,3-isthiocyanato ketones." Chemistry of Heterocyclic Compounds, 27: 339-341 (1991).
Forster, M.O., et al. "Studies in the Comphane Series. Part XXIV. Camphoryldithiocarbamic Acid and Camphorylthiocarbimide." Journal of the American Chemical Society, Chemical Society, Letchworth, GB., 91: 1877-1890 (Jan. 1, 1907).
Salvatore, R.N., et al. "Mild and efficient synthesis of thiocarbonates and thiocarbamates via a three-compnent coupling utilizing Cs2CO3 and TBAI." Tetrahedron Letter, 42: 2055-2058 (Mar. 11, 2001).
Bernabe, M., et al. "Dérivés du cyclopropane. V. Préparation d'acides amino-1 aryl-2 cyclopropanecarboxyliques et resultants preliminaries de leur interaction avec la dopadécarboxylase." European Journal of Medicinal Chemistry, Editions Scientifique Elsevier, Paris, FR., 14: 33-45 (Jan. 1, 1979).
Montanari, L., et al., "Sull-attività antifungina di diesteri del 2-mercapto benzenmetantiolo." Farmaco, Edizione Scientifica, Societa Chimica Italiana, Pavia, 37: 759-763 (Jan. 1, 1982) *Compound VII*.
Braun, J.V. "Mittheilungen über Dithiourethane." Chemische Berichte, Verlag Chemie GMBH, Weinheim, DE., 35(3): 3368-3388 (Oct. 1, 1902).

* cited by examiner

*Primary Examiner*—Rebecca L Anderson
*Assistant Examiner*—Jason M Nolan
(74) *Attorney, Agent, or Firm*—Robert C. Netter; Dann, Dorfman, Herrell & Skillman

(57) ABSTRACT

Novel indoleamine 2,3-dioxygenase (IDO) inhibitors, compositions comprising the same, and methods of use thereof are disclosed.

12 Claims, 7 Drawing Sheets

| Product | R₁ | R₂ | Yield (%) | Product | R₁ | R₂ | Yield (%) |
|---|---|---|---|---|---|---|---|
| 1 | 3-(indol-3-yl)methyl (25) | CH₃ | 43 | 10 | 4-fluorophenyl-(CH₂)₂– | CH₃ | 89 |
| 2 | 2-(indol-3-yl)ethyl (CH₂)₂– | CH₃ | 87 | 11 | PhCH₂CH₂N(CH₃)– =R¹-NH | CH₃ | 85 |
| 3 | 2-(benzothiophen-3-yl)ethyl | CH₃ | 22 | 12 | indol-3-ylmethyl (25) | H₂C=CH– | 52 |
| 4 | 3-(indol-3-yl)propyl (26) | CH₃ | 61 | 13 | indol-3-ylmethyl (25) | H₂C–Ph | 50 |
| 5 | 2-indanyl | CH₃ | 74 | 14 | indol-3-ylmethyl (25) | –(CH₂)₅CH₃ | 57 |
| 6 | adamantyl | CH₃ | 98 | 15 | 2-(indol-3-yl)ethyl | H₂C–Ph | 86 |
| 7 | 2-naphthylmethyl (28) | CH₃ | 54 | 16 | 2-(indol-3-yl)ethyl | 2-naphthylmethyl | 59 |
| 8 | benzyl | CH₃ | 74 | 17 | 2-(indol-3-yl)ethyl | 3-pyridylmethyl | 40 |
| 9 | phenethyl | CH₃ | 85 | 18 | 2-(indol-3-yl)ethyl | 4-pyridylmethyl | 50 |

Figure 2

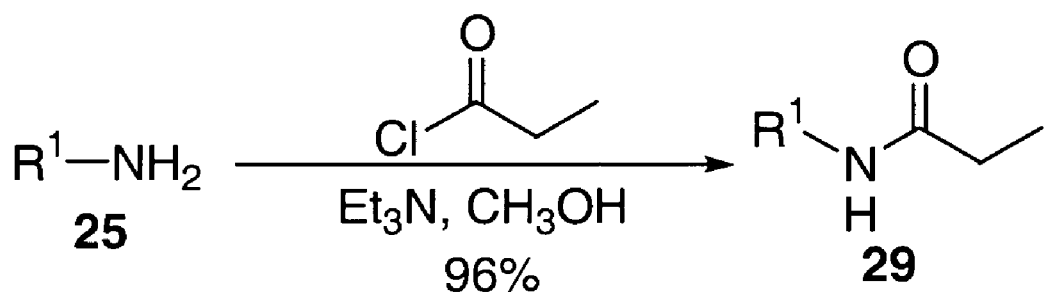
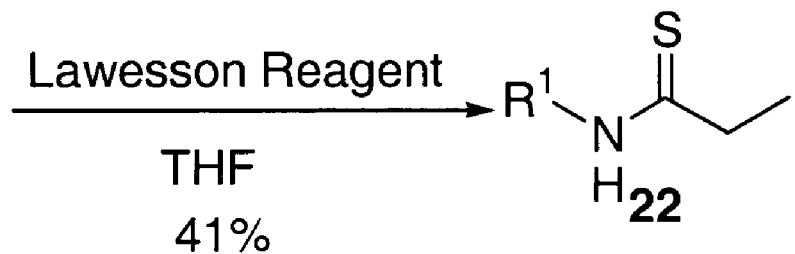
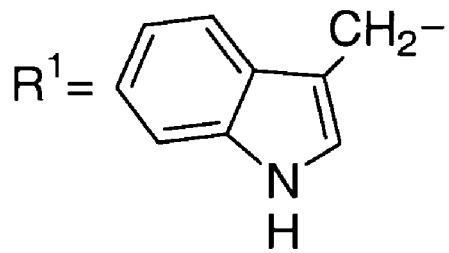
Figure 6

IDO INHIBITORS AND METHODS OF USE THEREOF

This application claims priority under 35 U.S.C. §119(e) to U.S. Provisional Patent Application No. 60/730,706, filed on Oct. 27, 2005. The foregoing application is incorporated by reference herein.

Pursuant to 35 U.S.C. Section 202 (c), it is acknowledged that the United States Government has certain rights in the invention described herein, which was made in part with funds from the National Cancer Institute Grant No. 1 R01 CA109542-01A1.

FIELD OF THE INVENTION

This invention relates to the field of oncology. Specifically, the invention provides novel chemotherapeutic agents and methods of using such agents for the treatment of cancer.

BACKGROUND OF THE INVENTION

Tumors characteristically express atypical, potentially immunoreactive antigens that are collectively referred to as tumor antigens. Accumulating evidence suggests that the failure of the immune system to mount an effective response against progressively growing tumors is not attributable to a lack of recognizable tumor antigens. Immunosuppression by tumors is poorly understood and mechanisms by which tumors may escape immune surveillance have been poorly explored. Recently, it has been shown that cytotoxic T cells become tolerized by a reduction in local concentrations of tryptophan that are elicited by indoleamine 2,3-dioxygenase (IDO; EC 1.13.11.42) activity. Furthermore, IDO has been implicated in tumor immunosuppression (Muller et al. (2005) Nat. Med., 11:312-9; Munn et al. (2004) Trends Mol. Med., 10:15-18; Uyttenhove et al. (2003) Nat. Med., 9:1269-74; Friberg et al. (2002) Intl. J. Cancer, 101:151-155).

Dietary catabolism of tryptophan is mediated by the structurally unrelated liver enzyme tryptophan dioxygenase (TDO2; 1.13.11.11). IDO is an extrahepatic oxidoreductase that catalyzes the initial and rate-limiting step in the degradation of tryptophan along the kynurenine pathway that leads to the biosynthesis of nicotinamide adenine dinucleotide (NAD$^+$) (Sono et al. (1996) Chem. Rev., 96:2841-87; Botting et al. (1995) Chem. Soc. Rev., 24:401-12; Sono et al. (1980) Biochem. Rev., 50:173-81). IDO is a monomeric 45 kDa heme-containing oxidase that is active with the heme iron in the ferrous (Fe$^{+2}$) form. The ferric (Fe$^{+3}$) form of IDO is inactive and substrate inhibition is believed to result from tryptophan (Trp) binding to ferric IDO (Sono et al. (1980) J. Biol. Chem., 255:1339-45; Kobayashi et al. (1989) J. Biol. Chem., 264:15280-3). The primary catalytic cycle of IDO does not involve redox changes, nevertheless IDO is prone to autooxidation and therefore a reductant is necessary to reactivate the enzyme. In vivo, IDO purportedly relies on a flavin or tetrahydrobiopterin co-factor. In vitro, methylene blue and ascorbic acid are believed to substitute for the natural flavin or tetrahydrobiopterin co-factor.

Inhibition of IDO has previously been targeted for other therapies, most notably neurological disorders (Botting et al. (1995) Chem. Soc. Rev., 24:401-12). Several metabolites of the kynurenine pathway are neurotoxic or are implicated in neurodegeneration, e.g. quinolinic acid, and therefore attention has focused on IDO. A recent review summarizes the range of compounds that have been tested as IDO inhibitors (Muller et al. (2005) Expert. Opin. Ther. Targets., 9:831-49).

SUMMARY OF THE INVENTION

In accordance with one aspect of the invention, novel inhibitors of indoleamine 2,3-dioxygenase (IDO) activity are provided. In a particular embodiment, the novel compounds have the formula:

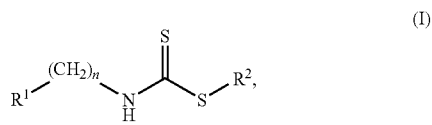

(I)

wherein $R^1$ is cycloalkyl, aryl, or

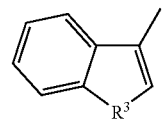

wherein $R^3$ is —NH—, —O—, or —S—; $R^2$ is alkenyl or —CH$_2$—R$^4$, wherein $R^4$ is hydrogen or aryl; and n is from 0 to about 3; with the proviso that the compound is not brassinin, N-[(Naphth-2-yl)methyl]-S-methyl-dithiocarbamate, or N-Benzyl-S-methyl-dithiocarbamate. In another embodiment, $R^4$ is selected from the group consisting of phenyl, naphthyl, and pyridyl. In yet another embodiment, $R^1$ is an aryl selected from the group consisting of indolyl, phenyl, naphthyl, indanyl, and adamantyl.

In another embodiment of the instant invention, compounds 2-6, 9-18, 20, 22-24, and 32, as described hereinbelow, are provided as novel IDO inhibitor. In a particular embodiment, the novel IDO inhibitors are selected from the group consisting of compounds 3-5, 12, 13, and 15-18.

According to another aspect of the present invention, methods are provided for treating cancer in a patient. The methods comprise administering an effective amount of a pharmaceutical composition comprising at least one IDO inhibitor in a pharmaceutically acceptable carrier medium, wherein at least one of the IDO inhibitors is selected from the group consisting of compounds 2-18, 20, 22-24, and 32 and compounds having the formula:

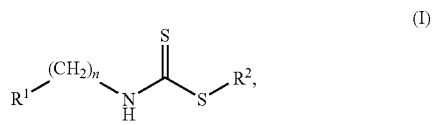

(I)

wherein $R^1$ is cycloalkyl, aryl, or

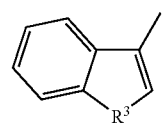

wherein $R^3$ is —NH—, —O—, or —S—; $R^2$ is alkenyl or —CH$_2$—R$^4$, wherein $R^4$ is hydrogen or aryl; and n is from 0 to about 3; with the proviso that the compound is not brassinin. In another embodiment, the method further comprises administering to the patient, concurrently or sequentially, an effective amount of at least one signal transduction inhibitor (STI) which may be administered in a pharmaceutically acceptable carrier. In still another embodiment of the invention, the method further comprises administering to the patient, concurrently or sequentially, an effective amount of at least one chemotherapeutic agent which may be in a pharmaceutically acceptable carrier.

In yet another embodiment of the present invention, methods are provided for treating a chronic viral infection in a patient in need thereof by administering to the patient, concurrently or sequentially, an effective amount of at least one indoleamine 2,3-dioxygenase (IDO) inhibitor and at least one chemotherapeutic agent.

In accordance with another aspect of the instant invention, pharmaceutical compositions comprising the above-described compounds are provided for administration in carrying out the above methods.

BRIEF DESCRIPTION OF THE DRAWINGS

FIG. 2 provides schemes for the synthesis of certain dithiocarbamates.

FIG. 6 provides a scheme for the synthesis of thioamide.

DETAILED DESCRIPTION OF THE INVENTION

Figure 1A:
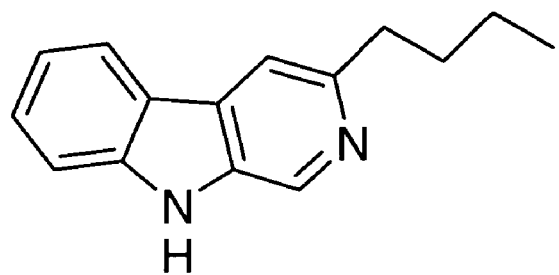
FIG. 1A shows the chemical structure of 3-butyl-β-carboline.
Figure 1B:
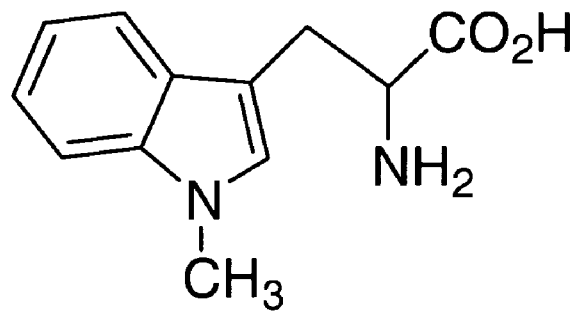
FIG. 1B shows the chemical structure of 1-methyl-tryptophan.

In accordance with the instant invention, a series of indole-based molecules were screened to determine their ability to inhibit IDO. Almost all previously known IDO inhibitors, whether competitive or non-competitive, possessed the indole ring of the natural substrate. Currently, the most potent IDO inhibitor reported is 3-butyl-β-carboline (FIG. 1A), a non-competitive inhibitor with a $K_i$=3.3 µM (Peterson et al. (1993) Med. Chem. Res., 3:473-82). However, the most commonly used IDO inhibitor is 1-methyl-tryptophan (FIG. 1B), a commercially available compound that is a competitive inhibitor with a $K_i$=34 µM (Cady et al. (1991) Arch. Biochem. Biophys., 291:326-33).

Figure 1C:
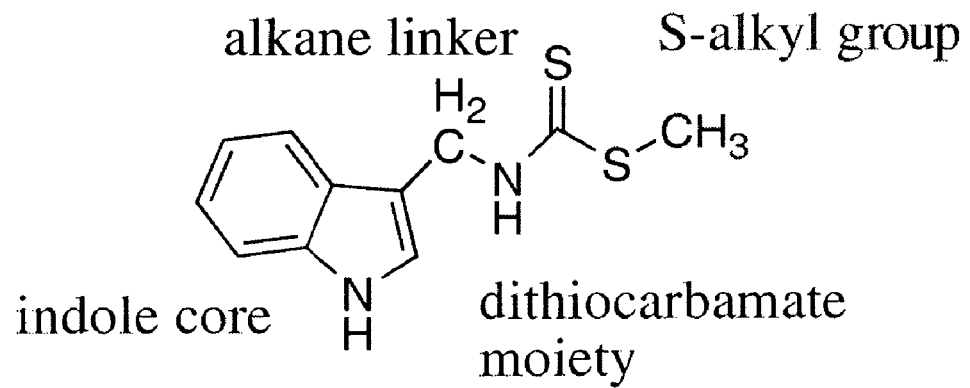
FIG. 1C shows the chemical structure of brassinin 1 and identifies the four components of brassinin.

The natural product brassinin (1, FIG. 1C) was determined to be a moderately active competitive IDO inhibitor, $K_i$=97.7 µM. Brassinin is a phytoalexin in the cruciferous plants and has demonstrated some anti-fungal and anti-cancer activity (Pedras et al. (2000) Phytochemistry, 53:161-76; Pedras et al. (2005) J. Org. Chem., 70:1828-34; Pedras et al. (1998) Phytochemistry, 49:1959-65; Mehta et al. (1995) Carcinogenesis, 16:399-404). Accordingly, a structure-activity relationship study of brassinin was performed with the goal of obtaining a more potent IDO inhibitor. The brassinin structure was divided into four components: the indole core, the alkane linker, the dithiocarbamate moiety and the S-alkyl group (FIG. 1C). Analogs of brassinin that varied each of the four components were synthesized to determine the effect of each component on the activity of the resulting structure. Substantially more potent inhibitors of IDO were developed in accordance with the instant invention.

Three interpretations that can be made from the systematic study of the IDO inhibitory activity of brassinin reported herein are as follows. Contrary to most previously reported IDO inhibitors, an indole ring was not necessary for inhibitory activity with the dithiocarbamate analogs of brassinin. Although indole-containing derivatives were still the most active inhibitors (i.e., 13 and 16) analogs such as 5, 7, 8 and 9, had significant inhibitory activity and provide new opportunities for further inhibitor development. Importantly, new analogs might be possible that avoid the pharmacological issues of the indole ring and leverage the wealth of chemical methods for benzene substitution. The dithiocarbamate moiety is an optimum group for IDO inhibition and probably chelates to the active site iron. Large unsaturated groups on the dithiocarbamate sulfur can be accommodated in the active site and lead to more potent inhibitors of IDO. Indeed, the new inhibitors (i.e. 13 and 16) are three times more potent than the most commonly used IDO inhibitor.

I. DEFINITIONS

The term "IDO inhibitor" refers to an agent capable of inhibiting the activity of indoleamine 2,3-dioxygenase (IDO) and thereby reversing IDO-mediated immunosuppression. An IDO inhibitor may be a competitive, noncompetitive, or irreversible IDO inhibitor. "A competitive IDO inhibitor" is a compound that reversibly inhibits IDO enzyme activity at the catalytic site (for example, without limitation, 1-methyl-tryptophan); "a noncompetitive IDO Inhibitor" is a compound that reversibly inhibits IDO enzyme activity at a non-catalytic site (for example, without limitation, norharman); and "an irreversible IDO inhibitor" is a compound that irreversibly destroys IDO enzyme activity by forming a covalent bond with the enzyme (for example, without limitation, cyclopropyl/aziridinyl tryptophan derivatives).

IDO inhibitors may include, without limitation, i) previously established (known) IDO inhibitors, including, but not limited to: 1-methyl-DL-tryptophan (1 MT; Sigma-Aldrich; St. Louis, Mo.), β-(3-benzofuranyl)-DL-alanine (Sigma-Aldrich), beta-(3-benzo(b)thienyl)-DL-alanine (Sigma-Aldrich), 6-nitro-L-tryptophan (Sigma-Aldrich), indole 3-carbinol (LKT Laboratories; St. Paul, Minn.), 3,3'-diindolylmethane (LKT Laboratories), epigallocatechin gallate (LKT Laboratories), 5-Br-4-Cl-indoxyl 1,3-diacetate (Sigma-Aldrich), 9-vinylcarbazole (Sigma-Aldrich), acemetacin (Sigma-Aldrich), 5-bromo-DL-tryptophan (Sigma-Aldrich), 5-bromoindoxyl diacetate (Sigma-Aldrich), and the IDO inhibitors provided in PCT/US04/05155 and PCT/US04/05154; and ii) the novel IDO inhibitors of the instant invention. In a preferred embodiment of the invention, the IDO inhibitors include the novel IDO inhibitors of the present invention.

A "signal transduction inhibitor" is an agent that selectively inhibits one or more vital steps in signaling pathways, in the normal function of cancer cells, thereby leading to apoptosis. Signal transduction inhibitors (STIs) include, but are not limited to, (i) bcr/abl kinase inhibitors such as, for example, STI 571 (Gleevec); (ii) epidermal growth factor (EGF) receptor inhibitors such as, for example, kinase inhibitors (Iressa, SSI-774) and antibodies (Imclone: C225 [Goldstein et al. (1995), Clin Cancer Res. 1:1311-1318], and Abgenix: ABX-EGF); (iii) her-2/neu receptor inhibitors such as, for example, Herceptin™ (trastuzumab); and farnesyl transferase inhibitors (FTI) such as, for example, L-744,832 (Kohl et al. (1995), Nat Med. 1(8):792-797); (iv) inhibitors of Akt family kinases or the Akt pathway, such as, for example, rapamycin (see, for example, Sekulic et al. (2000) Cancer Res. 60:3504-3513); (v) cell cycle kinase inhibitors such as, for example, flavopiridol and UCN-01 (see, for example, Sausville (2003) Curr. Med. Chem. Anti-Canc Agents 3:47-56); and (vi) phosphatidyl inositol kinase inhibitors such as, for example, LY294002 (see, for example, Vlahos et al. (1994) J. Biol. Chem. 269:5241-5248). In a particular embodiment, the STI is selected from the group consisting of STI 571, SSI-774, C225, ABX-EGF, trastuzumab, L-744,832, rapamycin, LY294002, flavopiridal, and UNC-01. In yet another embodiment, the STI is L-744,832.

The term "chemotherapeutic agent" refers generally to any compound that exhibits anticancer activity. Chemotherapeutic agents include, but are not limited to: alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nitroso ureas such as carmustine, lomustine, and streptozocin; platinum complexes such as cisplatin and carboplatin; bioreductive alkylators such as mitomycin, procarbazine, dacarbazine and altretamine); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, vinblastine, and paclitaxel (Taxol)); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide). Preferably, the chemotherapeutic agent is selected from the group consisting of: paclitaxel (Taxol®), cisplatin, docetaxol, carboplatin, vincristine, vinblastine, methotrexate, cyclophosphamide, CPT-11, 5-fluorouracil (5-FU), gemcitabine, estramustine, carmustine, adriamycin (doxorubicin), etoposide, arsenic trioxide, irinotecan, and epothilone derivatives.

A "therapeutically effective amount" of a compound or a pharmaceutical composition refers to an amount effective to prevent, inhibit, or treat the symptoms of a particular disorder or disease. For example, "therapeutically effective amount" may refer to an amount sufficient to modulate tumor growth or metastasis in an animal, especially a human, including without limitation decreasing tumor growth or size or preventing formation of tumor growth in an animal lacking any tumor formation prior to administration, i.e., prophylactic administration.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, excipient, auxilliary agent or vehicle with which an active agent of the present invention is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

"Concurrently" means (1) simultaneously in time, or (2) at different times during the course of a common treatment schedule.

"Sequentially" refers to the administration of one component of the method followed by administration of the other component. After administration of one component, the next component can be administered substantially immediately after the first component, or the next component can be administered after an effective time period after the first component; the effective time period is the amount of time given for realization of maximum benefit from the administration of the first component.

The term "cycloalkyl," as employed herein, includes cyclic hydrocarbon groups containing 1 to 3 rings which may be fused of unfused. Cycloalkyl groups may contain a total of 3 to 20 carbons forming the ring(s), preferably 6 to 10 carbons forming the ring(s). Optionally, one of the rings may be an aromatic ring as described below for aryl. Cycloalkyl groups may contain one or more double bonds. Each cycloalkyl group may be optionally substituted with 1 to about 4 substituents such as alkyl (an optionally substituted straight, branched or cyclic hydrocarbon group, optionally saturated, having from about 1-10 carbons, particularly about 1-4 carbons), halo (such as F, Cl, Br, I), haloalkyl (e.g., $CCl_3$ or $CF_3$), alkoxyl, alkylthio, hydroxy, methoxy, carboxyl, oxo, epoxy, alkyloxycarbonyl, alkylcarbonyloxy, amino, carbamoyl (e.g., $NH_2C(=O)$— or $NHRC(=O)$—, wherein R is an alkyl), urea (—$NHCONH_2$), alkylurea, and thiol. Exemplary cycloalkyls include, without limitation, indanyl and adamantyl.

"Alkenyl" refers to an unsubstituted or substituted hydrocarbon moiety comprising one or more carbon to carbon double bonds (i.e., the alkenyl group is unsaturated) and containing from 1 to about 12 carbon atoms or from 1 to about 5 carbon atoms, which may be a straight, branched, or cyclic hydrocarbon group. When substituted, alkenyl groups may be substituted at any available point of attachment. Exemplary substituents may include, but are not limited to, alkyl, halo, haloalkyl, alkoxyl, alkylthio, hydroxyl, methoxy, carboxyl, oxo, epoxy, alkyloxycarbonyl, alkylcarbonyloxy, amino, carbamoyl, urea, alkylurea, and thiol. Preferably, the alkenyl group comprises alternating double and single bonds such that bonds are conjugated. Exemplary alkenyl groups include, without limitation, allyl and 1,3-butadienyl.

The term "aryl," as employed herein, refers to monocyclic and bicyclic aromatic groups containing 6 to 10 carbons in the ring portion. Examples of aryl groups include, without limitation, phenyl, naphthyl, such as 1-naphthyl and 2-naphthyl, indolyl, and pyridyl, such as 3-pyridyl and 4-pyridyl. Aryl groups may be optionally substituted through available carbon atoms with 1 to about 4 groups. Exemplary substituents may include, but are not limited to, alkyl, halo, haloalkyl, alkoxyl, alkylthio, hydroxyl, methoxy, carboxyl, oxo, epoxy, alkyloxycarbonyl, alkylcarbonyloxy, amino, carbamoyl, urea, alkylurea, and thiol. The aromatic groups may be heteroaryl. "Heteroaryl" refers to an optionally substituted aromatic ring system that includes at least one, and preferably from 1 to about 4 sulfur, oxygen, or nitrogen heteroatom ring members.

II. NOVEL COMPOUNDS EXHIBITING IDO INHIBITORY ACTIVITY

In accordance with the instant invention, novel compounds are provided which are capable of inhibiting IDO activity and thereby suppressing tumor growth. In one embodiment, the novel IDO inhibitor has the formula:

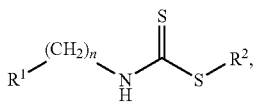

(I)

wherein $R^1$ is cycloalkyl, aryl, or

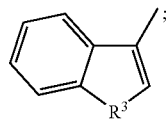

wherein $R^3$ is —NH—, —O—, or —S—; $R^2$ is alkenyl or —CH$_2$—$R^4$, wherein $R^4$ is hydrogen or aryl; and n is from 0 to about 3; with the proviso that the compound is not brassinin, N-[(Naphth-2-yl)methyl]-S-methyl-dithiocarbamate, or N-Benzyl-S-methyl-dithiocarbamate. In a particular embodiment, $R^4$ is selected from the group consisting of phenyl, naphthyl, and pyridyl. In another embodiment, $R^4$ is naphthyl. In another particular embodiment, n is 3. In yet another embodiment, $R^1$ is selected from the group consisting of indolyl, phenyl, naphthyl, indanyl and adamantyl. In still another embodiment, $R^1$ is indolyl.

In another embodiment of the invention, the novel IDO inhibitors are selected from the group consisting of compounds 2-6, 9-18, 20, and 22-24, described hereinbelow. In a particular embodiment, the novel IDO inhibitors are selected from the group consisting of compounds 3-5, 12, 13, and 15-18.

In still another embodiment, $R^2$ is:

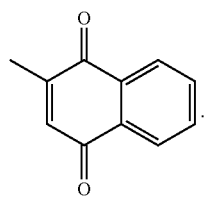

In a particular embodiment, the novel IDO inhibitor is

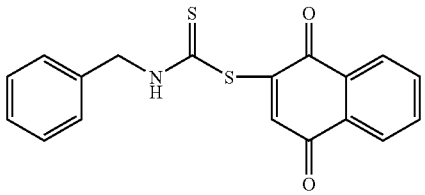

(32; N-benzyl-S-(naphthoquinon-2-yl)-dithiocarbamate).

III. THERAPIES AND COMPOSITIONS FOR THE TREATMENT OF CANCER AND VIRAL INFECTIONS

The present invention provides pharmaceutical compositions comprising at least one of the IDO inhibitors of the instant invention in a pharmaceutically acceptable carrier. Such a pharmaceutical composition may be administered, in a therapeutically effective amount, to a patient in need thereof for the treatment of cancer. The pharmaceutical compositions may comprise at least one IDO inhibitor of the instant invention in addition to at least one established (known) IDO inhibitor. In a specific embodiment, at least one of the IDO inhibitors of the pharmaceutical composition is selected from the group consisting of compounds of formula (I) and compounds 2-6, 9-18, 20, and 22-24.

Moreover, the present invention provides a method for the treatment of cancer by administering to a patient, in need thereof, a therapeutically effective amount of the compounds of the instant invention, preferably in the form of a pharmaceutical composition. In a particular embodiment, at least one the IDO inhibitors administered in the method of treating cancer is selected from the group consisting of compounds of formula (I) and compounds 2-18, 20, and 22-24.

The pharmaceutical composition may further comprise at least one signal transduction inhibitor (STI) (see, e.g., PCT/US04/05155 and PCT/US04/05154). Suitable STIs, as noted hereinabove, include, but are not limited to: (i) bcr/abl kinase inhibitors such as, for example, STI 571 (Gleevec); (ii) epidermal growth factor (EGF) receptor inhibitors such as, for example, kinase inhibitors (Iressa, SSI-774) and antibodies (Imclone: C225 [Goldstein et al. (1995), Clin Cancer Res. 1:1311-1318], and Abgenix: ABX-EGF); (iii) her-2/neu receptor inhibitors such as, for example, Herceptin™ (trastuzumab) and farnesyl transferase inhibitors (FTI) such as, for example, L-744,832 (Kohl et al. (1995), Nat Med. 1(8):792-797); (iv) inhibitors of Akt family kinases or the Akt pathway, such as, for example, rapamycin (see, for example, Sekulic et al. (2000) Cancer Res. 60:3504-3513); (v) cell cycle kinase inhibitors such as, for example, flavopiridol and UCN-01 (see, for example, Sausville (2003) Curr. Med. Chem. Anti-Canc Agents 3:47-56); and (vi) phosphatidyl inositol kinase inhibitors such as, for example, LY294002 (see, for example, Vlahos et al. (1994) J. Biol. Chem. 269:5241-5248). Alternatively, the at least one STI and the at least on IDO inhibitor may be in separate pharmaceutical compositions. In a specific embodiment of the present invention, the at least one IDO inhibitor and at least one STI may be administered to the patient concurrently or sequentially. In other words, the at least one IDO inhibitor may be administered first, the at least one STI may be administered first, or the at least one IDO inhibitor and the at least one STI may be administered at the same time. Additionally, when more than one IDO inhibitor and/or STI is used, the compounds may be administered in any order.

The pharmaceutical compositions of the invention may further comprise at least one chemotherapeutic agent. Suitable chemotherapeutic agents are described hereinabove. Preferred chemotherapeutic agents include, but are not limited to: paclitaxel (Taxol®), cisplatin, docetaxol, carboplatin, vincristine, vinblastine, methotrexate, cyclophosphamide, CPT-11, 5-fluorouracil (5-FU), gemcitabine, estramustine, carmustine, adriamycin (doxorubicin), etoposide, arsenic trioxide, irinotecan, and epothilone derivatives. In a particular embodiment, the chemotherapeutic agent is paclitaxel. As an alternative, the at least one chemotherapeutic agent and the at least on IDO inhibitor may be in separate pharmaceutical compositions. In a particular embodiment of the present invention, the at least one IDO inhibitor and at least one chemotherapeutic agent may be administered to the patient concurrently or sequentially. In other words, the at least one IDO inhibitor may be administered first, the at least one chemotherapeutic agent may be administered first, or the at least one IDO inhibitor and the at least one chemotherapeutic agent may be administered at the same time. Additionally, when more than one IDO inhibitor and/or chemotherapeutic agent and/or STI is used, the compounds may be administered in any order.

Cancers that may be treated using the present protocol include, but are not limited to: cancers of the prostate, colorectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma.

The present invention further provides a pharmaceutical composition for the treatment of a chronic viral infection in a patient comprising at least one IDO inhibitor, optionally, at least one chemotherapeutic drug, and, optionally, at least one antiviral agent, in a pharmaceutically acceptable carrier. The pharmaceutical compositions may comprise at least one IDO inhibitor of the instant invention in addition to at least one established (known) IDO inhibitor. In a specific embodiment, at least one of the IDO inhibitors of the pharmaceutical composition is selected from the group consisting of compounds of formula (I) and compounds 2-18, 20, and 22-24.

Also provided is a method for treating a chronic viral infection in a patient by administering an effective amount of the above pharmaceutical composition. In a particular embodiment, at least one of the IDO inhibitors administered in the method of treating a viral infection is selected from the group consisting of compounds of formula (I) and compounds 2-18, 20, and 22-24.

Suitable antiviral agents include, without limitation: acyclovir; gangcyclovir; foscarnet; ribavirin; and antiretrovirals such as, for example, nucleoside analogue reverse transcriptase inhibitors (e.g., azidothymidine (AZT), ddl, ddC, 3TC, d4T), non-nucleoside reverse transcriptase inhibitors (e.g., efavirenz, nevirapine), nucleotide analogue reverse transcriptase inhibitors, and protease inhibitors.

In a specific embodiment of the present invention, the at least one IDO inhibitor and at least one chemotherapeutic agent may be administered to the patient concurrently or sequentially. In other words, the at least one IDO inhibitor may be administered first, the at least one chemotherapeutic agent may be administered first, or the at least one IDO inhibitor and the at least one STI may be administered at the same time. Additionally, when more than one IDO inhibitor and/or chemotherapeutic agent is used, the compounds may be administered in any order. Similarly, any antiviral agent or STI may also be administered at any point in comparison to the administration of an IDO inhibitor.

The compounds of this combination treatment may also be administered for localized infections. Specifically, the at least one IDO inhibitor, optionally, at least one chemotherapeutic agent, and, optionally, at least one antiviral agent may be administered to treat skin infections such as shingles and warts. The compounds may be administered in any pharmaceutically acceptable topical carrier including, without limitation: gels, creams, lotions, ointments, powders, aerosols and other conventional forms for applying medication to the skin.

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, coxsackie virus, human immunodeficiency virus (HIV). Notably, parasitic infections (e.g., malaria) may also be treated by the above methods wherein compounds known to treat the parasitic conditions are optionally added in place of the antiviral agents.

In yet another embodiment, the pharmaceutical compositions comprising at least one IDO inhibitor of the instant invention may be administered to a patient to prevent arterial restenosis, such as after balloon endoscopy or stent placement. In a particular embodiment, the pharmaceutical composition further comprises at least one taxane (e.g., paclitaxel (Taxol); see e.g., Scheller et al. (2004) Circulation, 110:810-814).

IV. ADMINISTRATION OF PHARMACEUTICAL COMPOSITIONS AND COMPOUNDS

The pharmaceutical compositions of the present invention can be administered by any suitable route, for example, by injection, by oral, pulmonary, nasal or other modes of administration. In general, pharmaceutical compositions of the present invention, comprise, among other things, pharmaceutically acceptable diluents, preservatives, solubilizers, emulsifiers, adjuvants and/or carriers. Such compositions can include diluents of various buffer content (e.g., Tris-HCl, acetate, phosphate), pH and ionic strength; and additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol). The compositions can be incorporated into particulate preparations of polymeric compounds such as polylactic acid, polyglycolic acid, etc., or into liposomes. Such compositions may influence the physical state, stability, rate of in vivo release, and rate of in vivo clearance of components of a pharmaceutical composition of the present invention. See, e.g., Remington's Pharmaceutical Sciences, 18th Ed. (1990, Mack Publishing Co., Easton, Pa. 18042) pages 1435-1712 which are herein incorporated by reference. The pharmaceutical composition of the present invention can be prepared, for example, in liquid form, or can be in dried powder form (e.g., lyophilized).

In yet another embodiment, the pharmaceutical compositions of the present invention can be delivered in a controlled release system, such as using an intravenous infusion, an implantable osmotic pump, a transdermal patch, liposomes, or other modes of administration. In a particular embodiment, a pump may be used (see Langer, supra; Sefton, CRC Crit. Ref. Biomed. Eng. (1987) 14:201; Buchwald et al., Surgery (1980) 88:507; Saudek et al., N. Engl. J. Med. (1989) 321: 574). In another embodiment, polymeric materials may be employed (see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. (1983) 23:61; see also Levy et al., Science (1985) 228:190; During et al., Ann. Neurol. (1989) 25:351; Howard et al., J. Neurosurg. (1989) 71:105). In yet another embodiment, a controlled release system can be placed in proximity of the target tissues of the animal, thus requiring only a fraction of the systemic dose (see, e.g., Goodson, in Medical Applications of Controlled Release, supra, (1984) vol. 2, pp. 115-138). In particular, a controlled release device can be introduced into an animal in proximity to the site of inappropriate immune activation or a tumor. Other controlled release systems are discussed in the review by Langer (Science (1990) 249:1527-1533).

The following examples are provided to illustrate various embodiments of the present invention. These examples are not intended to limit the invention in any way.

Example 1

Synthesis of Compounds

All reactants and reagents were commercially available and were used without further purification unless otherwise indicated. Anhydrous THF was obtained by distillation from benzophenone-sodium under argon immediately before use. Anhydrous $CH_2Cl_2$ and $Et_3N$ were obtained by distillation from calcium hydride under argon. Methanol was dried over Mg and distilled under argon. A saturated solution of HCl in $CH_3OH$ was made by bubbling HCl through a drying tube, filled with $CaCl_2$, into a cooled flask of anhydrous $CH_3OH$ under a stream of argon. A saturated solution of $NH_3$ in $CH_3OH$ was made by bubbling anhydrous $NH_3$ into an Erlenmyer flask with a predetermined volume of $CH_3OH$. Concentrated refers to the removal of solvent with a rotary evaporator at normal water aspirator pressure followed by further evacuation with a two-stage mechanical pump unless otherwise indicated. Yields refer to chromatographically and spectroscopically pure (>95%) compounds, except as otherwise indicated. All new compounds were determined to be >95% pure by NMR, HPLC and/or GC. Melting points were determined using an open capillary and are uncorrected. $^1H$ and $^{13}C$ NMR spectra were recorded at 300 and 75 MHz, respectively. Chemical shifts are reported in δ values (ppm) relative to an internal reference (0.05% v/v) of tetramethylsilane (TMS) for $^1H$ NMR and the solvent peak in $^{13}C$ NMR, except where noted. Peak splitting patterns in the NMR are reported as follows: s, singlet; d, doublet; t, triplet; q, quartet; m, multiplet; br, broad. Rotamer peaks (about ¼ intensity) were seen for all dithiocarbamate structures (Holloway et al. (1967) Can. J. Chem., 45:2659-63). Normal phase HPLC (NP-HPLC) analysis was performed with UV detection at 254 nm and a 5µ silica gel column (250×4.6 mm); eluted with 90:10 n-hexane:IPA (or gradient) at 1 mL/min. Reverse phase HPLC (RP-HPLC) analysis was performed with UV detection at 254 nm and a $C_{18}$ column (300×3.9 mm); eluted with a gradient of $H_2O$+0.1% TFA and $CH_3CN$+0.1% TFA at 1 mL/min., unless otherwise indicated. GC analyses were performed with an EI-MS detector fitted with a 30 m×0.25 mm column filled with crosslinked 5% PH ME siloxane (0.25 µm film thickness); gas pressure 7.63 psi He. IR data was obtained with an FT-IR spectrometer. Thin layer chromatography was performed using silica gel 60 A precoated glass backed plates (0.25 mm thickness) with fluorescent indicator, which were scored and cut. Developed TLC plates were visualized with UV light (254 nm), iodine or $KMnO_4$. Flash column chromatography was conducted with the indicated solvent system using normal phase silica gel 60 A, 230-400 mesh. All reactions were carried out under an inert atmosphere of argon or nitrogen unless otherwise indicated.

Indole-3-methanamine (25). Indole-3-carboxaldehyde (189 mg, 1.3 mmol) and $NH_4OH.HCl$ (113 mg, 1.63 mmol) were dissolved in a Parr flask with 15 mL of MeOH, which was previously saturated with anhydrous ammonia. The flask was stoppered and placed on a Parr shaker for 5 hours. To the resulting solution was added 200 mg of Raney Nickel (50% slurry in $H_2O$) and the flask was pressurized to 60 psi with $H_2$ and allowed to shake overnight. The next day, the resulting mixture was filtered through celite and volatiles were removed to yield a yellow solid, 190 mg (100% yield). The product was unstable, so it was used immediately in subsequent reactions without further purification. $^1H$ NMR ($CDCl_3/CD_3OD$) δ 8.04 (br s, 1H, NH), 7.67 (d, 1H, ArH, J=7.8), 7.39 (d, 1H, ArH, J=7.1), 7.16 (3H, ArH), 4.07 (d, 2H, $ArCH_2$ J=7.4 Hz).

General Method for the Synthesis of Dithiocarbamates. The amine (1.0 eq.) was dissolved in pyridine (2-3 mL) and the solution was cooled to 0° C. (see FIG. 2). Triethylamine (1.0-1.1 eq) and carbon disulfide (1.1 eq) were added and the solution was stirred at 0° C. After 30 minutes, iodomethane (1.0-1.2 eq) was added and the reaction was allowed to slowly warm to room temperature overnight. The reaction was poured into 1 M $H_2SO_4$ and extracted with EtOAc (3×). The organic layer was washed with brine, dried with $Na_2SO_4$, and filtered. Concentration afforded a crude product that was chromatographed as described.

Brassinin (1)(Takasugi et al. (1988) Bull. Chem. Soc. Jpn., 61:285-89). Brassinin was formed from 25 according to the general method. The crude yellow solid was chromatographed on silica with EtOAc/hexanes (1:3) and the resulting yellow solid was further purified by recrystallization from $CH_2Cl_2$/hexanes to yield rose colored crystals (43% yd). m.p. 132-133° C. $^1H$ NMR ($CDCl_3$) δ 8.19 (br s, 1H, NH), 7.64 (d, 1H, ArH, J=7.9 Hz), 7.42 (d, 1H, ArH, J=8.1 Hz), 7.26 (m, 2H, ArH), 7.20 (m, 1H, ArH), 7.02 (br s, 1H, $CH_2NHC$), 5.06 (d, 2H, $ArCH_2$, J=4.5 Hz), 2.64 (s, 3H, $SCH_3$) and signals due to a minor rotamer (ca. 21%) at 4.79 (d, J=4.8 Hz), 2.75 (s). $^{13}C$ NMR (DMSO-$d_6$) δ 196.4, 136.2, 126.6, 125.0, 121.3, 118.8, 111.5, 110.2, 42.3, 17.4, and a signal due to a minor rotamer at 18.1. NP-HPLC r.t.=7.246 min. RP-HPLC r.t.=9.931 min.

N-[2-(Indol-3-yl)ethyl]-S-methyl-dithiocarbamate (2) (Pedras et al. (1998) J. Org. Chem., 63:416-7; Pedras et al. (2000) Can. J. Chem., 78:338-46). The general method was used with tryptamine and $CH_2Cl_2$ as the solvent. The crude product was chromatographed with $CH_2Cl_2$/hexanes (2:1) to afford a waxy yellow-white solid (87% yield). m.p.=59-64° C. $^1H$ NMR ($CDCl_3$) δ 8.05 (br s, 1H, NH), 7.61 (d, 1H, ArH, J=7.8 Hz), 7.36 (d, 1H, ArH, J=8.0 Hz), 7.22 (dt, 1H, ArH, J=8, 1 Hz), 7.14 (dt, 1H, ArH, J=8, 1 Hz), 7.01 (br s, 1H, NH), 4.05 (q, 2H, $CH_2NH$, J=12.4, 6.6 Hz), 3.11 (t, 2H, $ArCH_2$, J=6.7 Hz), 2.56 (s, 3H, $CH_3$) and signals due to a minor rotamer (ca. 29%) at 3.73 (m), 2.68 (s). $^{13}C$ NMR ($CDCl_3$) δ 198.8, 136.4, 127.1, 122.4, 122.1, 119.7, 118.7, 112.3, 111.3, 47.2, 23.9, 18.0, and signals due to a minor rotamer at 201.6, 126.8, 118.4, 46.1, 24.6, 18.9. GC: r.t.=15.00 min. EI-MS m/z (%) 202 (27, M$^+$-SCH$_3$), 143 (4), 130 (100). NP-HPLC r.t.=5.867 min.

N-[2-(benzo[b]thiophen-3-yl)ethyl]-S-methyl-dithiocarbamate (3). The general method was used with 2-(benzo[b]thiophen-3-yl)ethanamine and CH$_2$Cl$_2$ as the solvent. The crude product was chromatographed with EtOAc/hexanes (1:9) to yield a light amber oil which slowly crystallized (22% yield). m.p.=81-84° C. $^1$H NMR (CDCl$_3$) δ 7.90 (m, 1H, ArH), 7.79 (m, 1H, ArH), 7.43 (m, 3H, ArH), 7.02 (br s, 1H, NH), 5.18 (d, 2H, ArCH$_2$CH$_2$, J=4.17 Hz), 2.63 (m, 5H, SCH$_3$ overlapping with ArCH$_2$) and a signal due to a minor rotamer (ca. 17%) at 4.91 (m). $^{13}$C NMR (CDCl$_3$) δ 199.2, 140.6, 137.7, 130.7, 125.9, 124.9, 124.7, 123.1, 121.7, 45.1, 18.3, 14.2 and signals due to minor rotamer peaks at 60.4, 21.0. IR (KBr) ν$_{max}$ cm$^{-1}$: 3336, 3229, 3079, 2995, 2916, 1499, 1379, 1302, 1075, 926. NP-HPLC r.t.=4.774 min. RP-HPLC r.t.=12.110 min.

N-[3-(Indol-3-yl)propyl]-S-methyl-dithiocarbamate (4). The general method was used with 3-(indol-3-yl)-propan-1-amine, 2 eq. of Et$_3$N and MeOH as the solvent. After the reaction was complete, the volatiles were removed and the residue was dissolved in EtOAc (60 mL). The solution was washed with 0.5 M HCl (2×30 mL), H$_2$O (20 mL), and brine (20 mL). The organic solution was dried with Na$_2$SO$_4$, filtered and concentrated. The crude product was chromatographed with EtOAc/hexanes (1:3) to yield an off-white oil which crystallized overnight (61% yield). m.p.=54-56° C. $^1$H NMR (CDCl$_3$) δ 8.04 (br s, 1H, NH), 7.60 (d, 1H, ArH, J=7.6), 7.35 (d, 1H, ArH, J=8.0), 7.20 (m, 1H, ArH), 7.12 (m, 1H, ArH), 7.04 (m, 1H, ArH), 6.91 (br s, 1H, NH), 3.82 (q, 2H, ArCH$_2$CH$_2$CH$_2$, J=7.0 Hz), 2.86 (t, 2H, ArCH$_2$CH$_2$ J=7.2 Hz), 2.52 (s, 3H, SCH$_3$), 2.1 (m, 2H, ArCH$_2$CH$_2$) and signals due to a minor rotamer (ca. 30%) 3.50 (q, J=6.3 Hz), 2.68 (s). $^{13}$C NMR (CDCl$_3$) δ 198.7, 136.4, 127.1, 122.2, 121.6, 119.4, 118.7, 115.1, 111.3, 47.2, 28.3, 22.7, 18.0 and signals due to a minor rotamer at 46.0, 28.9, 18.7. IR (KBr) ν$_{max}$ cm$^{-1}$: 3410, 3321, 2919, 1888, 1504, 1337, 1094. EI-MS: m/z (%) 216 (57, M$^+$-SCH$_3$), 183 (5), 156 (10), 131 (23). NP-HPLC r.t.=12.331 min. RP-HPLC r.t.=11.865 min.

N-(Indan-2-yl)-S-methyl-dithiocarbamate (5). The general method was used with 2-aminoindan HCl. The crude product in EtOAc was decolorized with charcoal, filtered through celite and the volatiles were removed to yield a clear oil. The oil was chromatographed with EtOAc/hexanes (1:9) to yield an off-white solid (74% yield). m.p.=106-108° C. $^1$H NMR (CDCl$_3$) δ 7.23 (4H, ArH), 7.10 (br s, 1H, NH), 5.31 (m, 1H, CH$_2$CHCH$_2$), 3.44 (m, 2H, CHCHCH), 2.98 (dd, 2H, CHCHCH, J=16.5 Hz, 3.7 Hz), 2.62 (s, 3H, SCH$_3$) and signals due to a minor rotamer (ca. 38%) 4.78 (m), 2.70 (s). $^{13}$C NMR (CDCl$_3$) δ 198.6, 140.5, 127.0, 124.9, 57.9, 39.4, 18.2 and signals due to a minor rotamer at 57.1, 39.8, 18.5. IR (KBr) ν$_{max}$ cm$^{-1}$: 3226, 2948, 2916, 2088, 1483, 1371, 1337, 1070. NP-HPLC r.t.=4.509 min; RP-HPLC r.t.=12.160 min.

N-(Adamant-2-yl)-S-methyl-dithiocarbamate (6). The general method was used with 2-adamantylamine HCl and 2 eq. of Et$_3$N to afford a white solid (98% yield). m.p. 128-129° C. $^1$H NMR (CDCl$_3$) δ 7.25 (br s, 1H, NH), 4.65 (t, 1H, CHNH, J=3.6 Hz), 2.63 (s, 3H, SCH$_3$), 2.13 (m, 2H, CH$_2$), 1.73 (m, 12H, CH$_2$) and signals due to a minor rotamer (ca. 36%) 4.08 (m), 2.68 (s). $^{13}$C NMR (CDCl$_3$) δ 197.8, 97.5, 61.1, 37.3, 32.7, 31.4, 27.4, 18.5 and signals due to a minor rotamer at 37.8, 32.0, 27.3, 19.3. IR (KBr) ν$_{max}$ cm$^{-1}$: 3351, 2918, 2852, 1497, 1384, 1117, 942. NP-HPLC r.t.=4.138 min. RP-HPLC r.t.=13.233 min.

N-[(Naphth-2-yl)methyl]-S-methyl-dithiocarbamate (7) (Pedras et al. (2004) Phytochemistry, 65:2685-2694). The general method was used with 28, 2 eq. of Et$_3$N and MeOH as the solvent. The crude product was chromatographed on silica with EtOAc/hexanes (15:85) to yield a yellow solid (54% yield). m.p. 70-72° C. $^1$H NMR (CDCl$_3$) δ 7.79 (m, 3H, ArH), 7.68 (s, 1H, ArH), 7.47 (2H, ArH). 7.38 (1H, ArH), 7.22 (br s, 1H, NH), 5.01 (d, 2H, ArCH$_2$, J=5.2), 2.61 (s, 3H, SCH$_3$) and a signal due to a minor rotamer (ca. 23%) 4.67 (d, J=5.6 Hz). $^{13}$C NMR (CDCl$_3$) δ 199.4, 133.7, 133.5, 133.0, 128.8, 127.9, 127.8, 126.6, 126.3, 126.0, 51.4, 18.4 and signals due to a minor rotamer at 50.8, 19.0. IR (KBr) ν$_{max}$ cm$^{-1}$: 3340, 3203, 3052, 2918, 1922, 1505, 1305, 1085. EI-MS m/z (%) 199 (36, M$^+$-SCH$_3$), 141 (100), 115 (31). NP-HPLC r.t.=4.168 min. RP-HPLC r.t.=12.456 min.

N-Benzyl-S-methyl-dithiocarbamate (8) (Mohanta et al. (2000) Tetrahedron, 56:629-637; Burrows et al. (1952) J. Chem. Soc. Abs., 4118-22; Thorn et al. (1962) *The Dithiocarbamates and Related Compounds*; Elsevier: New York, 1962, p. 78). The general method was used with benzylamine and the crude product was chromatographed with EtOAc/hexanes (1:10) to yield an off-white oil (74% yield). $^1$H NMR (CDCl$_3$) δ 7.34 (5 overlapping H, ArH), 7.09 (br s, 1H, NH), 4.92 (d, 2H, ArCH$_2$, J=5.1), 2.66 (s, 3H, SCH$_3$) and signals due to a minor rotamer (ca. 22%) 4.64 (d, J=5.5 Hz), 2.71 (s). $^{13}$C NMR (CDCl$_3$) δ 199.2, 136.3, 129.0, 128.3, 128.2, 51.3, 18.3. IR (KBr) ν$_{max}$ cm$^{-1}$: 3338, 3238, 3028, 2917, 1953, 1656, 1504, 1378, 1090. NP-HPLC r.t.=4.323 min. RP-HPLC r.t.=11.342 min.

N-Phenethyl-S-methyl-dithiocarbamate (9). The general method was used with phenethylamine and the crude product was chromatographed with EtOAc/hexanes (1:10) to yield an off-white solid (85% yield). m.p. 50-51° C. $^1$H NMR (CDCl$_3$) δ 7.28 (5 overlapping H, ArH), 6.91 (br s, 1H, NH$_2$), 4.02 (t, 2H, ArCH$_2$CH$_2$, J=6.9), 2.98 (t, 2H, ArCH$_2$CH$_2$, J=7.0), 2.61 (s, 3H, SCH$_3$) and signals due to a minor rotamer (ca. 24%) at 3.71 (m), 2.69 (s). $^{13}$C NMR (CDCl$_3$) δ 199.1, 138.2, 128.8, 128.7, 126.8, 48.0, 34.2, 18.1 and signals due to a minor rotamer at 47.3, 34.9, 18.5. IR (KBr) ν$_{max}$ cm$^{-1}$: 3340, 3240, 3026, 2918, 1946, 1496, 1337, 1095. NP-HPLC r.t.=4.580 min. RP-HPLC r.t.=11.467 min.

N-4-Fluorophenethyl-S-methyl-dithiocarbamate (10). The general method was used with 4-fluorophenethylamine and the solvent was CH$_2$Cl$_2$. The volatiles were removed and the residue was dissolved in EtOAc. The organic layer was washed with 1 M H$_2$SO$_4$ (40 mL), H$_2$O (40 mL) and brine (30 mL). The resulting organic solution was dried with Na$_2$SO$_4$ and filtered. The volatiles were removed to yield a beige solid which was chromatographed with EtOAc/hexanes (8/92) to yield a white solid (89% yield). m.p. 59-60° C. $^1$H NMR (CDCl$_3$) δ 7.18 (m, 2H, ArH), 7.01 (m, 2H, ArH), 3.96 (q, 2H, ArCH$_2$CH$_2$, J=7.0 Hz), 2.96 (t, 2H, ArCH$_2$, J=7.1 Hz), 2.62 (s, 3H, SCH$_3$) and signals due to a minor rotamer (ca. 24%) at 3.69 (q, J=6.6 Hz), 2.68 (s). $^{13}$C NMR (CDCl$_3$) δ 199.4, 161.8 (d, J=243 Hz), 133.9, 130.2, 115.8, 48.0, 33.5, 18.1 and signals due to a minor rotamer at 130.1, 47.2, 30.9, 18.5. IR (KBr) ν$_{max}$ cm$^{-1}$: 3250, 3002, 2921, 1886, 1506, 1385, 1222, 940.8. NP-HPLC r.t.=5.105 min. RP-HPLC r.t.=11.646 min.

N,S-Dimethyl-N-phenethyldithiocarbamate (11). The general method was used with N-methylphenethylamine and the solvent was CH$_2$Cl$_2$. The crude product was chromatographed with EtOAc/hexanes (1/19) to yield a white oil (85% yield). $^1$H NMR (CDCl$_3$) δ 7.29 (m, 5H, ArH), 4.25 (t, 2H, ArCH$_2$CH$_2$, J=6.9 Hz), 3.20 (s, 3H, NCH$_3$), 3.01 (q, 2H, ArCH$_2$, J=6.8 Hz), 2.66 (s, 3H SCH$_3$) and signals due to a minor rotamer (ca. 42%) at 3.89 (m), 3.47 (s). $^{13}$C NMR (CDCl$_3$) δ 198.6, 138.9, 138.1, 129.3, 129.2, 129.1, 127.0, 59.5, 40.9, 32.9, 20.7 and signals due to a minor rotamer at 56.6, 44.6, 34.0. IR (KBr) $v_{max}$ cm$^{-1}$: 3025, 2917, 1949, 1808, 1485, 1386, 1292, 1185, 1100, 992.5. NP-HPLC r.t.=4.238 min. RP-HPLC r.t.=12.700 min.

S-Allyl-brassinin (12). The general method was used with 25, but allyl bromide was substituted for iodomethane. The crude product was purified by chromatography on silica with EtOAc/hexanes (3/7) to afford an orange oil (52% yield). $^1$H NMR (CDCl$_3$) δ 8.17 (br s, 1H, NH), 7.64 (d, 1H, ArH, J=7.8 Hz), 7.43 (d, 1H, ArH, J=8.1 Hz), 7.21 (3H, ArH), 7.03 (br s, 1H, NH), 5.93 (m, 1H, SCH$_2$CH=CH$_2$), 5.22 (m, 2H, SCH$_2$CH=CH$_2$), 5.05 (d, 2H, ArCH$_2$, J=4.4 Hz), 3.92 (d, 2H, SCH$_2$CH=CH$_2$, J=7.7 Hz) and signals due to a minor rotamer (ca. 16%) at 4.69 (m), 4.09 (d, J=7 Hz). $^{13}$C NMR (CDCl$_3$) δ 196.3, 136.2, 132.7, 126.4, 122.7, 120.2, 118.6, 118.5, 111.5, 110.3, 43.1, 38.3 and signals due to a minor rotamer at 41.0, 39.5. IR (KBr) $v_{max}$ cm$^{-1}$: 3402, 2915, 1852, 1635, 1377, 1063. NP-HPLC r.t.=6.723 min. RP-HPLC r.t.=11.640 min.

S-Benzyl-brassinin (13). The general method was used with 25, but benzyl bromide was substituted for iodomethane and CH$_2$Cl$_2$ was used as the solvent. The crude product was chromatographed on silica EtOAc/hexanes (3/7) to yield a translucent, yellow oil which slowly solidified. Recrystallization from CH$_2$Cl$_2$/hexanes yielded a bright yellow solid (50% yield). m.p. 101-102° C. $^1$H NMR (CDCl$_3$) δ 8.22 (br s, 1H, NH), 7.62 (d, 1H, ArH, J=7.9 Hz), 7.28 (9H, ArH+PhH), 6.98 (br s, 1H, NH), 5.11 (d, 2H, ArCH$_2$, J=3.9 Hz), 4.55 (s, 2H, CH$_2$Ph) and signals due to a minor rotamer (ca. 19%) at 4.77 (d, J=4.5 Hz), 4.67 (s). $^{13}$C NMR (CDCl$_3$) δ 196.4, 136.6, 136.3, 129.0, 128.6, 127.5, 126.5, 124.0, 122.8, 120.3, 118.7, 111.4, 110.7, 43.2, 39.9. IR (KBr) $v_{max}$ cm$^{-1}$: 3.417, 3334, 3058, 1890, 1494, 1455, 1067. NP-HPLC, r.t.=6.798 min. RP-HPLC, r.t.=12.452 min.

S-Hexyl-brassinin (14). The general method was used with 25, but 1-iodohexane was substituted for iodomethane. The crude product was chromatographed on silica with EtOAc/hexanes (3/7) to yield a golden oil (57% yield). $^1$H NMR (CDCl$_3$) δ 8.18 (br s, 1H, NH), 7.65 (d, 1H, ArH, J=7.8 Hz), 7.43 (d, 1H, ArH, 8.1 Hz), 7.22 (3H, ArH), 6.99 (br s, 1H, NH), 5.06 (d, 2H, ArCH$_2$, J=4.4 Hz), 3.26 (t, 2H, SCH$_2$, J=7.5 Hz), 1.70 (m, 2H, SCH$_2$CH$_2$CH$_2$CH$_2$CH$_2$CH$_3$), 1.39 (6H, SCH$_2$CH$_2$CH$_2$CH$_2$CH$_2$CH$_3$), 0.88 (t, 3H, CH$_3$, J=7.5 Hz) and signals due to a minor rotamer (ca. 19%) at 4.79 (d, J=4.8 Hz), 3.39 (t, J=7.5 Hz). $^{13}$C NMR (CDCl$_3$) δ 197.6, 136.2, 126.4, 124.0, 122.6, 120.1, 118.6, 111.5, 110.5, 43.0, 35.4, 29.0, 28.5, 22.5, 14.0 and signals due to a minor rotamer at 42.0, 36.5. IR (KBr) $v_{max}$ cm$^{-1}$: 3409, 3328, 2955, 2927, 2855, 1620, 1494, 1456, 1379, 1094. NP-HPLC r.t.=5.962 min. RP-HPLC r.t.=13.823 min.

N-[2-(indol-3-yl)ethyl]-S-benzyl-dithiocarbamate (15). The general method was used with tryptamine as the amine and CH$_2$Cl$_2$ as the solvent. Benzyl bromide was used as the alkylating agent in place of iodomethane. The crude product was chromatographed with EtOAc/hexanes (1:4) to yield white crystals (86% yield). Further purification was accomplished by recrystallization in EtOAc/hexanes to afford a 73% yield. m.p.=79-81° C. $^1$H NMR (CDCl$_3$) δ 8.02 (br s, 1H, NH), 7.58 (m, 1H, ArH), 7.37 (m, 6H, ArH), 7.32–7.18 (m, 1H, ArH), 7.13 (t, 1 H, ArH, J=9.0 Hz), 6.99 (m, 2H, ArH), 4.48 (s, 2H, SCH$_2$), 4.05 (q, J=6.0 Hz, 1H, ArCH$_2$CH$_2$), 3.09 (m, 2H, ArCH$_2$), and signals due to a minor rotamer (ca. 24%) at 4.59 (s), 3.74 (q, J=6.0 Hz). $^{13}$C NMR (CDCl$_3$) δ 197.2, 136.5, 136.3, 129.3, 128.9, 128.6, 127.6, 127.4, 127.1, 122.4, 122.1, 119.7, 118.7, 112.2, 111.3, 47.2, 39.8, 24.6, 23.9, and signals due to a minor rotamer at 135.7, 127.6, 118.4, 41.0, 24.6. IR (KBr) $v_{max}$ cm$^{-1}$: 3394, 3179, 1618, 1503, 1455, 1332, 1095, 936. EI-MS: m/z (%) 130 (100), 202 (37). GC: r.t. 14.81 minutes. NP-HPLC: r.t. 7.61 min. RP-HPLC: r.t. 12.87 min. Anal. Calcd for C$_{18}$H$_{18}$N$_2$S$_2$: C, 66.22; H, 5.56; N, 8.58; S, 19.64. Found: C, 66.19; H, 5.43; N, 8.42; S, 19.87.

N-[2-(indol-3-yl)ethyl]-S-[(naphth-2-yl)methyl]-dithiocarbamate (16). The general method was used with tryptamine as the amine and CH$_2$Cl$_2$ as the solvent. 2-(Bromomethyl)naphthalene was used as the alkylating agent in place of iodomethane. The crude product was chromatographed with EtOAc/hexanes (1:4) to afford the pure product (59% yield). Further purification was accomplished by recrystallization in EtOAc/hexanes to afford white crystals (29% yield). m.p.=158-160° C. $^1$H (CDCl$_3$) δ 8.05 (br s, 1H, NH), 7.90 (m, 1H, ArH), 7.79 (t, J=9.4 Hz, 4H, ArH), 7.46 (m, 5H, ArH), 7.11-7.35 (m, 4H, ArH), 6.97 (s, 1H, ArH), 4.64 (s, 2H, SCH$_2$), 4.08 (q, ArCH$_2$CH$_2$, J=6.0 Hz), 3.12 (t, 2H, ArCH$_2$, J=6.0 Hz), and signals due to a minor rotamer (ca. 25%) at 4.77 (s), 3.78 (q, J=6.0 Hz). $^{13}$C (CDCl$_3$) δ 197.3, 136.6, 134.2, 133.5, 132.9, 128.7, 128.0, 127.9, 127.3, 127.2, 126.5, 126.2, 122.6, 122.4, 119.9, 118.9, 112.5, 111.5, 47.4, 40.3, 24.1, 1.2 and signals due to a minor rotamer (ca. 20%) at δ 46.0, 42.0. IR (KBr) $v_{max}$ cm$^{-1}$: 3436, 3191, 2914, 2837, 1592, 1515, 1451, 1387, 1358, 1326, 1300, 1204, 1089, 999, 935, 816, 736. EI-MS: m/z (%) 130 (100), 202 (24). GC: r.t. 14.66 minutes. NP-HPLC: r.t. 5.70 min. RP-HPLC: r.t. 13.2 min.

N-[2-(indol-3-yl)ethyl]-S-[(pyrid-3-yl)methyl]-dithiocarbamate (17). The general method was used with tryptamine as the amine and CH$_2$Cl$_2$ as the solvent. 3-(Bromomethyl)pyridine, HBr salt, was used as the alkylating agent in place of iodomethane and 2.0 eq. of Et$_3$N were used. The crude product was chromatographed with EtOAc/hexanes (3:1) to afford a powdery tan solid (21% yield). m.p.=° C. $^1$H NMR (CDCl$_3$) 8.5 (m, 2H, ArH), δ 8.16 (br s, 1H), 7.69 (m, 1H, ArH), 7.58 (t, 1H, ArH, J=6.0 Hz), 7.37 (d, 1H, ArH, J=6.0 Hz), 7.24 –7.12 (m, 4H, ArH), 7.03 (m, 1H, ArH), 4.52 (s, 2H, SCH$_2$), 4.08 (m, 2H, ArCH$_2$CH$_2$), 3.12 (m, 2H, ArCH$_2$), and signals due to a minor rotamer (ca. 25%) at 4.58 (s), 3.75 (m). $^{13}$C NMR (CDCl$_3$) δ 197.0, 150.3, 148.8, 136.8, 133, 127, 123.6, 122.7, 122.4, 120, 118.9, 112.5, 111.6, 53.5, 47.7, 36.9, 24.2 and a signal due to a minor rotamer at 54.0. IR (KBr) $v_{max}$ cm$^{-1}$: 3403, 3306, 3164, 2917, 1724, 1619, 1500, 1455, 1421, 1392, 1332, 1257, 1089, 926, 851, 739. EI-MS: m/z (%) 130 (100), 202 (35). GC: r.t. 14.78 min. NP-HPLC: r.t. 27.90 min. RP-HPLC: r.t. 9.39 min.

N-[2-(indol-3-yl)ethyl]-S-[(pyrid-4-yl)methyl]-dithiocarbamate (18). The general method was used with tryptamine as the amine and CH$_2$Cl$_2$ as the solvent. 4-(Bromomethyl)pyridine, HBr salt, was used as the alkylating agent in place of iodomethane and 2.0 eq. of Et$_3$N were used. The crude product was recrystallized with EtOAc/hexanes (3:1) to afford tan crystals (50% yield). m.p.=125-7° C. $^1$H NMR (CDCl$_3$) 8.51 (m, 2H, ArH), 8.08 (br s, 1H), 7.59 (m, 1H, ArH), 7.39 (d, 1H, ArH, J=6.9 Hz), 7.28-7.00 (m, 6H, ArH), 4.51 (s, 2H, SCH$_2$), 4.07 (m, ArCH$_2$CH$_2$, J=6.0 Hz), 3.14 (m, 2H, ArCH$_2$), and signals due to a minor rotamer (ca. 25%) at 4.60 (s), 3.75 (m). $^{13}$C NMR (CDCl$_3$) δ 196.3, 150.1, 146.7, 136.7, 127.4, 124.3, 124.1, 122.7, 122.4, 120.0, 118.9, 112.5, 111.6, 47.9, 38.5, 24.2, 19.8. IR (KBr) $v_{max}$ cm$^{-1}$: 3404, 3299, 2917, 2851, 2178, 2099, 1600, 1508, 1455, 1416, 1337, 1225, 1091, 1002, 927, 743. EI-MS: m/z (%) 130 (100), 202 (29). GC: r.t. 14.70 min. NP-HPLC: r.t. 28.90 min. RP-HPLC: r.t. 9.40 min.

Figure 4:
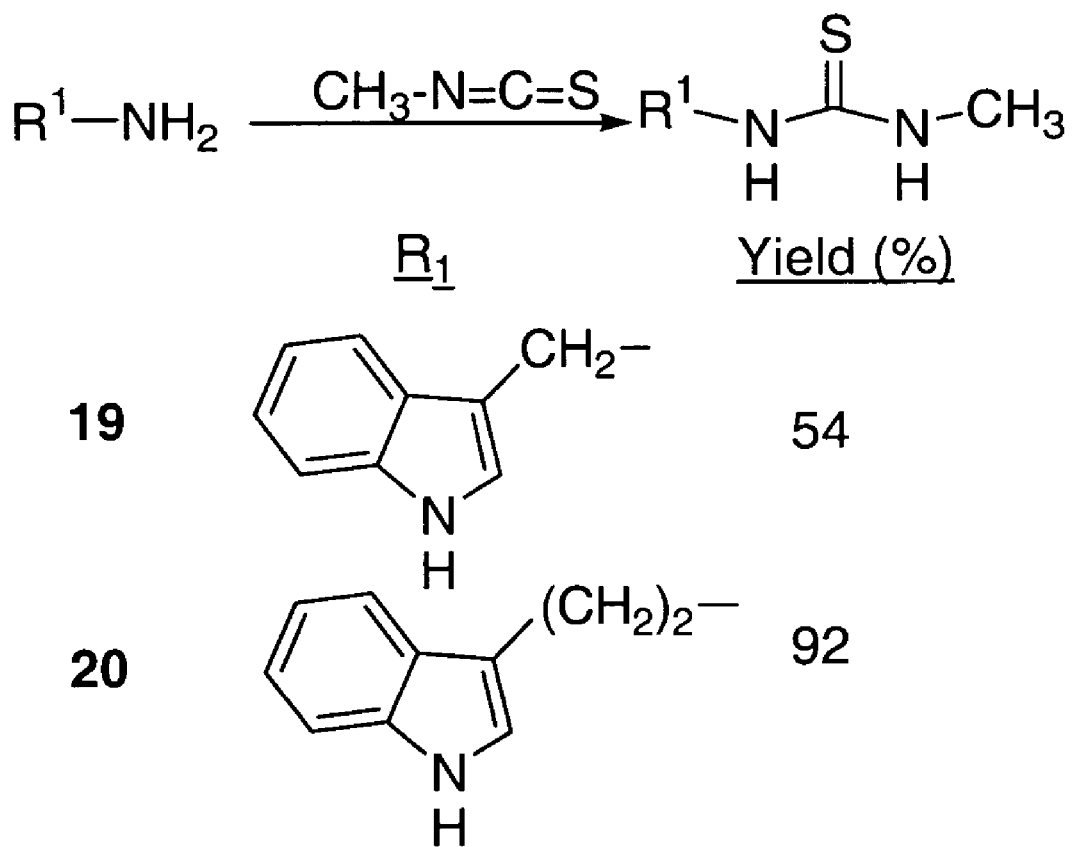
FIG. 4 provides a scheme for the synthesis of thioureas.

General Method for the Synthesis of Thioureas (See FIG. 4). The amine was dissolved/suspended in CH$_2$Cl$_2$, cooled to 0° C. and treated with Et$_3$N (2.1-2.2 eq). Methyl isothiocyanate (1.1-1.5 eq) was added about 5 min. later and the reaction was allowed to slowly warm to room temperature while stirring overnight.

N-[1-(Indol-3-yl)methyl]-N'-methyl-thiourea (19). The general method was used with 25. The volatiles were removed from the reaction and the crude residue was recrystallized from EtOAc/hexanes to yield a gold, crystalline solid (54% yield). m.p. 148-150° C. $^1$H NMR (DMSO-$d_6$) δ 10.9 (br s, 1H, NH), 7.65 (m, 1H, ArH), 7.36 (m, 2H, ArH), 7.10 (t, 1H, ArH, J=7.2 Hz), 4.75 (br s, 2H, ArCH$_2$), 2.85 (br s, 3H, NHCH$_3$). $^{13}$C NMR (DMSO-$d_6$) δ 183.4, 137.1, 124.9, 124.4, 122.1, 119.4, 112.7, 111.9, 40.1 (overlapped with CDCl$_3$), 31.5. IR (KBr) $v_{max}$ cm$^{-1}$: 3210, 1565, 1456, 1300, 1089. NP-HPLC (isocratic) r.t.=23.949 min. NP-HPLC (gradient) r.t.=22.493 min.

N-[1-(Indol-3-yl)ethyl]-N'-methyl-thiourea (20). The general method was used with tryptamine HCl. The crude product was isolated by washing the reaction mixture with 1 M H$_2$SO$_4$ (2×), saturated NaHCO$_3$, and brine and drying with Na$_2$SO$_4$. After concentration, the crude product was further purified by chromatography with EtOAc/hexanes (gradient, 1/1 to 3/1) to afford an oil which crystallizes on sitting to a light brown solid (92% yield). m.p.=102-6° C. $^1$H NMR (CDCl$_3$) δ 8.13 (s, 1H, NH), 7.60 (d, 1H, ArH, J=7.8 Hz), 7.37 (d, 1H, ArH, J=8.1 Hz), 7.21 (t, 1H, ArH, J=7.0 Hz), 7.12 (t, 1H, ArH, J=7.0 Hz), 7.04 (s, 1H, ArH), 5.75 (br s, 2H, NH—C=S), 3.79 (br d, 2H, ArCH$_2$CH$_2$, J=5.4 Hz), 3.06 (t, 2H, ArCH$_2$, J=6.6 Hz), 2.79 (br d, 3H, CH$_3$, J=4.5 Hz). $^{13}$C NMR (CDCl$_3$) δ 182.3, 136.3, 127.1, 122.4, 122.3, 119.6, 118.5, 112.4, 111.4, 44.8, 30.5, 24.8. IR (KBr) $v_{max}$ cm$^{-1}$: 3394, 3320, 3323, 3051, 1561, 1342. NP-HPLC r.t.=24.240 min. RP-HPLC (1/1 MeOH/H$_2$O) r.t.=6.098 min.

Brassitin (21) (Monde et al. (1995) Phytochemistry, 39:581-6) (See FIG. 5). Freshly made 25 (190 mg, 1.3 mmol) and Et$_3$N (271 µL, 1.95 mmol) was dissolved in anhydrous MeOH (10 mL). The flask was cooled to 0° C. and methyl chlorothioformate (116 µL, 1.36 mmol) was added dropwise followed by stirring at room temperature for 6 hours. A few drops of H$_2$O were added to quench excess reagent and the volatiles were evaporated. The residue was dissolved in EtOAc (35 mL) and washed with 0.5 M HCl (2×20 mL), sat. NaHCO$_3$ (20 mL), and brine (15 mL). The organic solution was dried with Na$_2$SO$_4$, filtered and concentrated to afford a crude brownish-orange solid (270 mg). After recrystallization from CH$_2$Cl$_2$/hexanes, beige crystals: 125 mg, 44% yd. mp 110-111° C. $^1$H NMR (CDCl$_3$) δ 8.15 (br s, 1H, NH), 7.64 (d, 1H, ArH J=7.9), 7.39 (d, 1H, ArH J=7.1), 7.23 (m, 1H, ArH), 7.18 (m, 1H, ArH), 7.13 (m, 1H, ArH), 5.52 (br s, 1H, CH$_2$NHC), 4.67 (d, 2H, ArCH$_2$, J=5.1), 2.38 (s, 3H, SCH$_3$). $^{13}$C NMR (CDCl$_3$) δ 167.6, 136.3, 126.3, 123.3, 122.5, 119.9, 118.7, 112.1, 111.3, 36.9, 12.4. EI-MS m/z (%) 220 (37, M+), 205 (9), 172 (12, M$^+$-SCH$_3$), 130 (100). NP-HPLC r.t.=9.827 min. RP-HPLC (1/1 CH$_3$CN/H$_2$O+0.1% TFA) r.t.=9.512 min.

N-[(Indol-3-yl)methyl]propanamide (29) (See FIG. 6). Compound 25 (1.00 g, 6.84 mmol) and Et$_3$N (1.4 mL, 10.26 mmol) were dissolved in MeOH and cooled to 0° C. Propionyl chloride (633 mg, 6.84 mmol) was added dropwise and the reaction was stirred at room temperature for 4 hours. The volatiles were removed and the residue was taken up in CH$_2$Cl$_2$ (40 mL), washed with 10% citric acid (20 mL), satd. NaHCO$_3$ (20 mL) and brine (20 mL). The organic layer was dried with Na$_2$SO$_4$, filtered and the volatiles were removed to yield 1.33 g of a white, crystalline solid (1.33 g, 96% yield). An analytical sample was recrystallized from EtOAc/hexanes. m.p.=91-92° C. $^1$H NMR (CDCl$_3$) δ 8.80 (br s, 1H, NH), 7.62 (d, 1H, ArH, J=7.85 Hz), 7.38 (d, 1H, ArH, J=7.2 Hz), 7.20 (3H, ArH), 5.80 (br s, 1H, NH), 4.60 (d, 2H, ArCH$_2$, J=5.1 Hz), 2.20 (q, 2H, COCH$_2$CH$_3$, J=7.6 Hz), 1.14 (t, 3H, COCH$_2$CH$_3$, J=7.6 Hz). $^{13}$C NMR (CDCl$_3$) δ 173.6, 136.5, 126.6, 123.3, 122.5, 119.9, 118.8, 112.8, 111.4, 35.2, 29.7, 9.9. IR (KBr) $v_{max}$ cm$^{-1}$: 3405, 1891, 1634, 1532, 1097.

N-[(Indol-3-yl)methyl]propanethioamide (22). Amide 29 (190 mg, 0.94 mmol) was dissolved in THF (20 mL). Lawesson reagent (304 mg, 0.75 mmol) was added to the resulting solution and the reaction was stirred for 2 h at room temperature. The volatiles were removed and the residue was dissolved in CH$_2$Cl$_2$ (20 mL) and washed with H$_2$O (12 mL). The organic layer was dried with Na$_2$SO$_4$ and filtered. After standing, a white precipitate formed which was filtered and the filtrate concentrated. The resulting residue (380 mg) was chromatographed with EtOAc/hexanes (1:1) to yield a clear oil which slowly crystallizes (85 mg, 41% yield). m.p. 132-134° C. $^1$H NMR (CDCl$_3$) δ 8.23 (br s, 1H, NH), 7.63 (1H, ArH), 7.41 (1H, ArH), 7.23 (3H, ArH), 4.98 (d, 2H, ArCH$_2$, J=4.5 Hz), 2.68 (q, 2H, CSCH$_2$CH$_3$, J=7.5 Hz), 1.30 (t, 3H, CSCH$_2$CH$_3$, J=7.5 Hz). $^{13}$C NMR (CDCl$_3$) δ 205.9, 136.3, 126.5, 124.0, 122.8, 120.3, 118.7, 111.5, 110.8, 42.2, 40.0, 13.5. IR (KBr) $v_{max}$ cm$^{-1}$: 3331, 2975, 2931, 1523, 1413, 1090. EI-MS m/z (%) 218 (49, M$^+$), 163 (8), 131 (12), 130 (100). NP-HPLC r.t.=10.894 min. RP-HPLC r.t.=10.402 min.

2-Naphthoyl chloride. A 100 mL round bottom flask was charged with 2-naphthoic acid (2 g, 11.6 mmol) and SOCl$_2$ (15 mL). The solution was refluxed for 4 hours and then concentrated to yield a yellow solid which was used without further purification (2.21 g, 100% yield); $^1$H NMR (CDCl$_3$) δ 8.76 (s, 1H, ArH), 8.04 (2H, ArH), 7.93 (d, 2H, ArH, J=8.9 Hz), 7.66 (m, 2H, ArH).

2-Naphthamide (27) (See FIG. 3). 2-Naphthoyl chloride (2.21 g, 11.6 mmol) was dissolved in a MeOH/NH$_3$ solution (2 M, 20 mL) and was allowed to stir overnight. Volatiles were removed and the resulting white solid was triturated with EtOAc. The solid was filtered and washed with cold EtOAc to yield a white solid which was used without further purification (1.98 g, 100% yield). m.p. 191-192° C. $^1$H NMR (CDCl$_3$) δ 8.39 (s, 1H, ArH), 7.90 (4H, ArH), 7.57 (m, 2H, ArH). $^{13}$C NMR (CDCl$_3$) δ 169.3, 135.0, 132.6, 130.5, 129.0, 128.6, 128.1, 127.9, 127.8, 126.9, 123.7. IR (nujol) $v_{max}$ cm$^{-1}$: 3400, 3210, 1650, 1628, 1512, 1510.

2-Aminomethylnaphthalene (28). Compound 27 (1.00 g, 5.8 mmol) in THF (20 mL) was added slowly to a solution of LAH (1.76 g, 46.4 mmol) in THF (45 mL) at 0° C. The solution was allowed to warm to room temperature and the reaction was stirred overnight. The reaction was cooled to 0° C. and quenched with H$_2$O. The solids were filtered from the solution through celite and washed with hot THF. The filtrate was concentrated and the residue was dissolved in EtOAc (80 mL) and washed with 1 M HCl (3×30 mL). The aqueous layer was basified with 6 M NaOH to a pH of 12 and the precipitate was extracted with EtOAc (3×30 mL). The resulting organic solution was washed with brine (40 mL), dried with Na$_2$SO$_4$ and filtered. Concentration afforded a slightly yellow solid (510 mg, 56% yield). m.p. 55-56° C. $^1$H NMR (CDCl$_3$) δ 7.80 (3H, ArH), 7.72 (s, 1H, ArH), 7.43 (m, 3H, ArH), 4.00 (s, 2H, ArCH$_2$). $^{13}$C NMR (CDCl$_3$) δ 140.6, 133.5, 132.5, 128.2, 127.7, 126.1, 125.8, 125.5, 125.1, 46.6. IR (KBr) $v_{max}$ cm$^{-1}$: 3362, 3291, 3050, 2915, 1950, 1596, 1507, 1358, 1273. GC: r.t.=8.97 min. EI-MS m/z (%) 157 (83, M$^+$), 156 (100), 141 (15), 129 (49), 128 (40), 127 (24), 115 (10).

Figure 7:
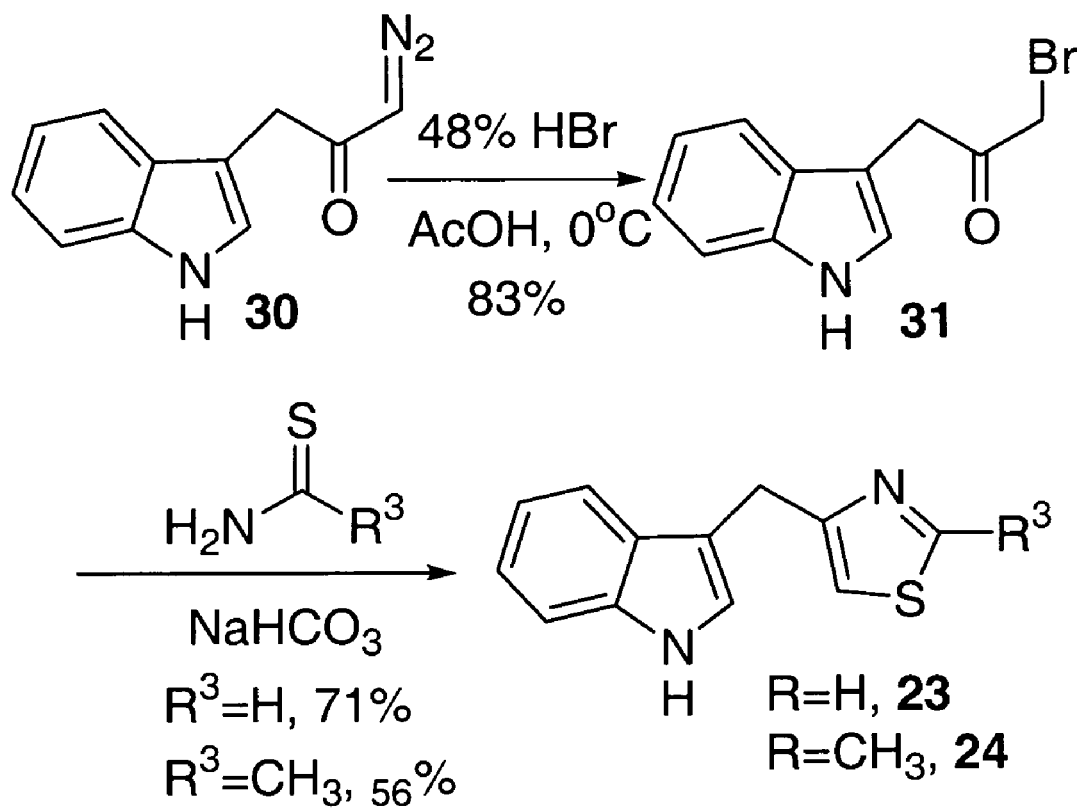
FIG. 7 provides a scheme for the synthesis of thiazole.

1-Bromo-3-(indol-3-yl)propanone (31) (See FIG. 7). The diazoketone 30 (379 mg, 1.90 mmol) was dissolved in acetic acid (4 mL) and cooled to 0° C. HBr (48%, 0.51 mL) was added dropwise. Forty minutes later the reaction was diluted with H$_2$O and then quenched at 5° C. with saturated NaHCO$_3$. The reaction mixture was extracted with CH$_2$Cl$_2$ (2×), washed with saturated. NaHCO$_3$, H$_2$O, brine, dried with Na$_2$SO$_4$, filtered and concentrated to a brown oil (398 mg, 83% yield). The crude product was used immediately in the next step. $^1$H NMR (CDCl$_3$) δ 8.26 (br s, 1H, NH), 7.56 (d, 1H, ArH, J=7.8 Hz), 7.39 (d, 1H, ArH, J=7.8 Hz), 7.27-7.13 (m, 3H, ArH), 4.07 (s, 2H, CH$_2$Br), 3.95 (s, 2H, ArCH$_2$).

General Method for the Synthesis of Thiazoles. Compound 31 was dissolved in EtOH and treated with thioamide (1.5 eq) and NaHCO$_3$ (1.5 eq). The resulting mixture was heated at reflux overnight. Upon cooling the reaction material was partitioned between EtOAc and half saturated NaHCO$_3$. The aqueous layer was extracted with EtOAc and the combined organic layers were washed with H$_2$O and brine, dried with MgSO$_4$, filtered and concentrated to a brown oily solid. The crude thiazole product was purified by chromatography with EtOAc/hexanes (1:2).

4-[(Indol-3-yl)methyl]thiazole (23). The general method was used with thioformamide to afford a 71% yield (Londergan et al. (1953) J. Am. Chem. Soc., 75:4456-8). $^1$H NMR (CDCl$_3$) δ 8.76 (d, 1H, SCHN, J=2.0 Hz), 8.11 (br s, 1H, NH), 7.52 (d, 1H, ArH, J=7.6 Hz), 7.36 (d, 1H, ArH, J=8.0 Hz), 7.18 (t, 1H, ArH, J=7.1 Hz), 7.08 (t, 2H, ArH, J=7.4 Hz), 6.90 (s, 1H, ArH), 4.34 (s, 2H, ArCH$_2$). $^{13}$C NMR (CDCl$_3$) δ 157.5, 152.5, 122.5, 122.1, 119.4, 119.1, 113.8, 113.5, 111.2, 27.6. IR (CH$_2$Cl$_2$) $v_{max}$ cm$^{-1}$: 3626, 3470, 3051, 2987, 1420, 1264. GC: r.t.=15.05 min. EI-MS m/z (%) 214 (100, M$^+$), 213 (86), 186 (15), 154 (14), 130 (51). RP-HPLC (1/1 CH$_3$CN/H$_2$O+0.1% TFA) r.t.=4.408 min.

4-[(Indol-3-yl)methyl]-2-methyl-thiazole (24). The general method was used with thioacetamide to afford a 56% yield. $^1$H NMR (CDCl$_3$) δ 8.17 (br s, 1H, NH), 7.53 (d, 1H, ArH, J=7.8 Hz), 7.34 (d, 1H, ArH, J=8.1 Hz), 7.17 (t, 1H, ArH, J=7.0 Hz), 7.10-7.04 (m, 2H, ArH), 6.63 (s, 1H, ArH), 4.23 (s, 2H, CH$_2$), 2.69 (s, 3H, CH$_3$). $^{13}$C NMR (CDCl$_3$) δ 165.6, 162.3, 156.1, 136.4, 127.3, 122.6, 122.0, 119.3, 119.1, 113.4, 111.1, 27.7, 19.1. IR (KBr) $v_{max}$ cm$^{-1}$: 3247, 3090, 2919, 1527, 1454, 1429, 1188. GC: r.t.=15.40 min. EI-MS m/z (%) 228 (100, M$^+$), 227 (71), 186 (22), 154 (23), 130 (39). RP-HPLC (1/1 MeOH/H$_2$O) r.t.=18.60 min.

N-benzyl-S-(naphthoquinon-2-yl)-dithiocarbamate) (32). To a suspension of benzylamine hydrochloride (300 mg, 1.87 mmoles) in CH$_2$Cl$_2$ (5 mL) at 0° C. was added NEt$_3$ (208.4 mg, 2.05 mmoles) and the reaction mixture was stirred for 15 minutes followed by the addition of CS$_2$ (142.5 mg, 1.87 mmoles). After 30 minutes, 1,4-naphthoquinone (296.1 mg, 1.87 mmoles) was added and the reaction was allowed to slowly warm to rt overnight. The reaction was poured into 1 M H$_2$SO$_4$ and extracted with EtOAc (3×50 mL). The organic layer was washed with brine, dried with Na$_2$SO$_4$, and filtered. Concentration afforded a crude product that was chromatographed (CHCl$_3$/EtOAc/Hexanes, 1:1:2) to afford a brick red solid (125 mg, 20% yield).

Example 2

Inhibition of IDO

Figure 3:
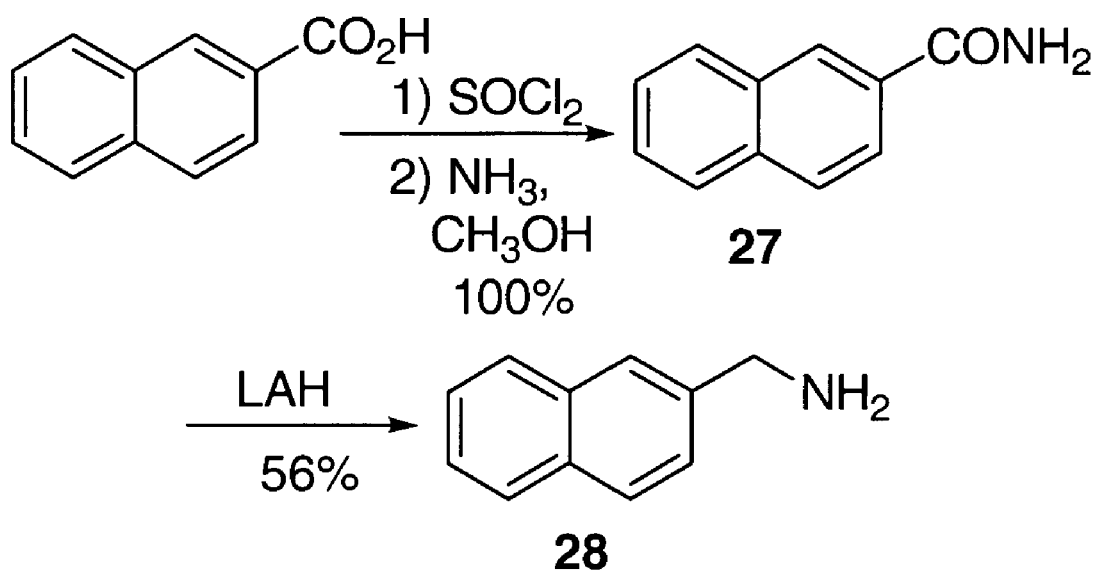
FIG. 3 provides a scheme for the synthesis of 2-aminomethyl-napthalene.

Brassinin dithiocarbamate analogs were synthesized by adding an amine to carbon disulfide at 0° C., stirring for one hour, and then adding an alkyl halide. Modification of the indole core or alkane linker occurred by substituting different amines. Certain amines were commercially available while others required synthesis as described hereinabove. The indole-3-methanamine 25 of brassinin 1 was prepared through the reductive amination of indole-3-carboxaldehyde. Although there are several different reductive amination procedures reported in the literature, the procedure described in Mehta et al. was determined to be the most effective (Mehta et al. (1995) Carcinogenesis, 16:399-404; Schallenberg et al. (1983) Z. Naturforsch, 38b:108-12; Yamada et al. (1993) Heterocycles, 36:2783-2804; Kutschy et al. (1998) Tetrahedron, 54:3549-66). Homotryptamine 26, the amine reagent for 4, was synthesized in three steps from indole-3-propanoic acid following literature precedent (Dornyei et al. (2002) Coll. Czech. Chem. Comm., 67:1669-80). 2-Aminomethyl-naphthalene 28 was also synthesized in three steps from 2-naphthoic acid (FIG. 2). Modifications of the S-alkyl piece occurred by substituting various alkyl halides for iodomethane, e.g. 12-18 (FIG. 3).

Figure 5:
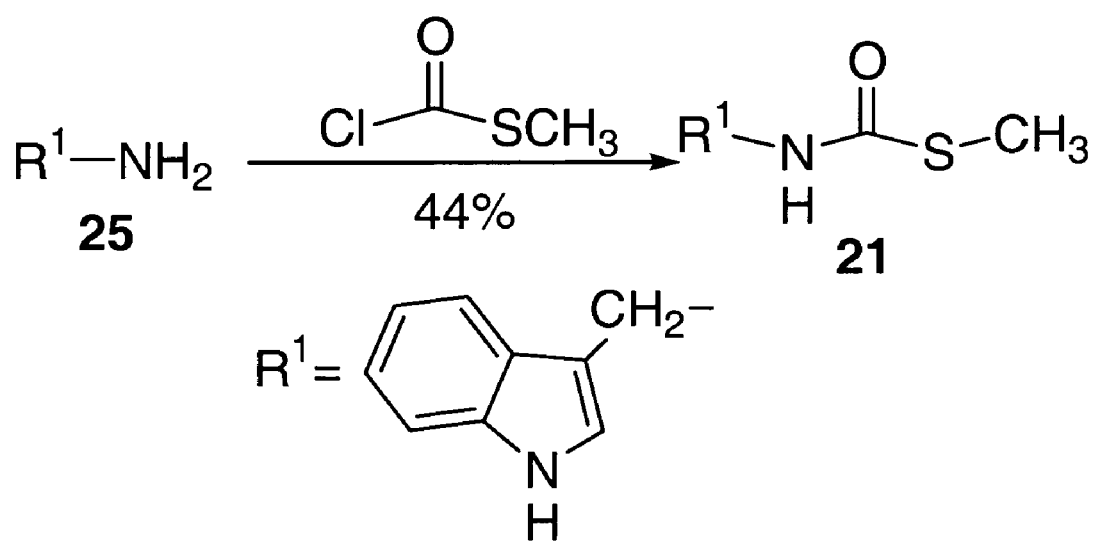
FIG. 5 provides a scheme for the synthesis of brassitin.

Modifications to the dithiocarbamate moiety included thioureas (19 and 20, FIG. 4), S-alkyl thiocarbamates (21, FIG. 5), thioamides (22, FIG. 6) and thiazoles (23 and 24, FIG. 7). The thioureas were synthesized by reacting amines with methyl isothiocyanate (FIG. 4). The S-alkyl thiocarbamate 21, a phytoalexin called brassitin, came from the reaction of S-alkyl thiochloroformate with 25 (FIG. 5). The thioamide 22 was synthesized by reaction of 25 with an acid chloride and then treatment with Lawesson's reagent (FIG. 6). Thiazoles were synthesized by reaction of thioformamide or thioacetamide with α-bromoketones 27 (FIG. 7). The α-bromoketones 31 were generated from the corresponding α-diazoketone derivative 30, which was synthesized in three steps from indole-3-acetic acid following a literature procedure (Lutz et al. (1947) J. Org. Chem., 12:767-70; Cuevas-Yanez et al. (2004) Tetrahedron, 60:1505-1511).

Brassinin analogs were analyzed for inhibition of extracted and purified Y-interferon-induced human IDO. The assay was conducted according to a literature protocol, with ascorbic acid and methylene blue serving the role of reductant (Littlejohn et al. (2000) Protein Expression and Purification, 19:22-29; Sono et al. (1989) J. Biol. Chem., 264:1616-1622). Catalase was added to prevent IDO decomposition from peroxide side products (Ohnishi et al. (1977) J. Biol. Chem., 252:4643-4647). The enzyme assay monitored for formation of N-formylkynurenine by hydrolyzing the formyl group and spectrophotometrically analyzing for the conjugated imine generated from kynurenine and 4-(dimethylamino) benzaldehyde.

Specifically, the inhibition assays were performed in a 96-well microtiter plate as previously described with a small modification (Littlejohn et al. (2000) Prot. Expr. Purif., 19:22-29). Briefly, the reaction mixture contained 50 mM potassium phosphate buffer (pH 6.5), 40 mM ascorbic acid, 400 μg/ml catalase, 20 μM methylene blue and purified recombinant IDO (1) optimized based on its activity. The reaction mixture was added to the substrate, L-tryptophan (L-Trp), and the inhibitor. The L-Trp was serially diluted from 200 to 25 μM and the inhibitors were tested at two concentrations, 200 and 400 μM. The reaction was carried out at 37° C. for 60 minutes and stopped by adding 30% (w/v) trichloroacetic acid. The plate was heated at 65° C. for 15 minutes to convert formylkynurenine to kynurenine and then was spun at 6000 g for 5 minutes. Finally 100 μl supernatant from each well was transferred to a new 96 well plate and mixed with 2% (w/v) p-dimethylamino-benzaldehyde in acetic acid. The yellow color generated from the reaction with kynurenine was measured at 490 nm using a Synergy HT microtiter plate reader (Bio-Tek, Winooski, Vt.). The data was analyzed using Graph Pad Prism 4 software (Graph Pad Software Inc., San Diego, Calif.).

In all cases where inhibition was seen, the brassinin analogs demonstrated competitive inhibition. The inhibitory constants shown are an average of two or three trials. The array of analogs tested allowed for an evaluation of the four components of the brassinin structure and resulted in some important discoveries

TABLE 1

IDO inhibition data.

| Compound | $K_i$ (μM) |
|---|---|
| 1 | 97.7 |
| 2 | 82.54 |
| 3 | 40.95 |
| 4 | 33.97 |
| 5 | 42.06 |
| 6 | 179.6 |
| 7 | 47.57 |
| 8 | 72.41 |
| 9 | 62.36 |
| 10 | 149.35 |
| 11 | 1267 |
| 12 | 36.95 |
| 13 | 13.22 |
| 14 | 363.6 |
| 15 | 17.15 |
| 16 | 11.55 |
| 17 | 28.38 |
| 18 | 20.48 |
| 19 | N.I.[a] |
| 20 | 342.3 |
| 21 | N.I. |
| 22 | 202 |
| 23 | 1292 |
| 24 | 328.7 |

[a]N.I. = no inhibition detected.

Surprisingly, a large range of substitutions could be made in the analogs tested which still retained some IDO inhibitory activity. Indeed, not only were flat aromatic structures (e.g. 5, 7-10) effective substitutes, but the adamantyl structure 6 could also bind in the substrate pocket, based on the competitive inhibition witnessed for all these analogs. Although IDO is relatively promiscuous, there are still very few reports of substrates or inhibitors that lack the indole core (Muller et al. (2005) Expert. Opin. Ther. Targets., 9:831-49). The current demonstration of inhibition with benzene and cycloalkyl based structures expands the range of structures that behave as IDO inhibitors. Furthermore, benzene aromatic structures are more easily derivatized with available synthetic methods than indole compounds. Indole derivatives can also be a liability given the neuroactivity of some indole containing compounds, e.g., serotonin and related indolealkylamines.

Linker variation was possible and, in the brassinin series, it was found that the longer linker lead to more potent compounds, c.f. 1 vs. 2 vs. 4. However, analogs that modified two brassinin components may not replicate this trend (c.f. 13 vs. 15). Taken together the results with the alkane linker modifications and the indole core changes indicate the IDO active site is rather accommodating.

The most interesting results came from isosteric modifications of the dithiocarbamate. The transformation of brassinin's dithiocarbamate moiety to a thiourea (19, 20), thiocarbamate (21), thioamide (22) or thiazole (23, 24) led to weaker or no inhibition. Notably the S-methyl-thiocarbamate analog 21 (brassitin), suffered a complete loss in inhibitory activity with the substitution of a carbonyl for the thiocarbonyl group. Given the recognized metal coordinating properties of dithiocarbamates, it is likely that the dithiocarbamate moiety is chelating to the heme iron at the active site of IDO (Thomas et al. (2001) J. Immunol., 166:6332-40; Warshawsky et al. (2001) Langmuir, 17:5621-35; Diaz et al. (2000) Tox. Sci., 55:284-92; Paleologos et al. (2002) Anal. Chim. Acta, 458: 241-8; Furuta et al. (2002) Biochem. J., 365:639-48; Iseki et al. (2000) Biochem. Biophys. Res. Comm., 276:88-92; Kim et al. (1999) J. Neurochem., 72:1586-92). Interestingly, there is a report of IDO acceleration in the presence of diethyldithiocarbamate wherein the acceleration results from inhibition of superoxide dismutase which can remove superoxide, an IDO activator (Taniguchi et al. (1977) J. Biol. Chem., 252:2774-6). In fact, pyrrolidine dithiocarbamate, reportedly inhibits IDO, besides being a well-known anti-oxidant and NF-kB inhibitor (Thomas et al. (2001) J. Immunol., 166: 6332-40; Nurmi et al. (2004) J. Neurochem., 91:755-65; Hayakawa et al. (2003) EMBO J., 22:3356-66; Liu et al. (1997) J. Immunol., 159:3976-83; Ziegler-Heitbrock et al. (1993) J. Immunol., 51:6986-93; Schreck et al. (1992) J. Exp. Med., 175:1181-94).

The greatest increases in potency were realized in modifications of the S-alkyl group. Although alkyl groups that were longer than the methyl in brassinin were less active, S-allyl brassinin 12 was two times more potent than brassinin and the benzyl analog 13 was almost one order of magnitude more potent. Moreover, the tryptamine/naphthyl analog 16 was as potent as 13; pyridyl analogs 17 and 18 also demonstrated modest inhibition. Since all these compounds behaved as competitive inhibitors, these analogs reveal a large additional pocket in the IDO active site capable of accommodating flat, aromatic groups.

It has reported that β-carboline, a non-competitive inhibitor, binds to the heme iron at the active site, but not in the same space as the substrate (Sono et al. (1989) Biochemistry, 28:5392-5399). Moreover, the β-carboline reportedly acts as a nitrogen donor ligand and competes with $O_2$ for binding to the heme iron. It is possible that the large aromatic S-alkyl pieces are binding in the same pocket that accommodates the tricyclic aromatic β-carboline structure. Nevertheless, the pyridyl analogs 17 and 18 failed to demonstrate stronger inhibition despite their similarity to the pyridyl ring of β-carboline.

Several publications and patent documents are cited in the foregoing specification in order to more fully describe the state of the art to which this invention pertains. The disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A compound having indoleamine 2,3 dioxygenase (IDO) inhibitory activity, said compound having the formula of:

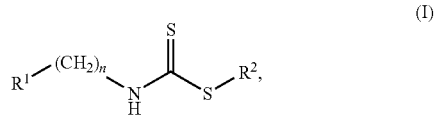

wherein R¹ is

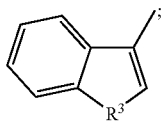

wherein R³ is —NH—, —O—, or —S—; R² is alkenyl or —CH₂—R⁴, wherein R⁴ is hydrogen or aryl; and n is from 0 to 3; with the proviso that the compound is not brassinin.

2. The compound of claim 1, wherein R⁴ is selected from the group consisting of phenyl, naphthyl, and pyridyl.

3. The compound of claim 1 selected from the group consisting of N-[2-(Indol-3-yl)ethyl]-S-methyl-dithiocarbamate; N-[2-(benzo[b]thiophen-3-yl)ethyl]-S-methyl-dithiocarbamate; N-[3-(Indol-3-yl)propyl]-S-methyl-dithiocarbamate; S-Allyl-brassinin; S-Benzyl-brassinin; S-Hexyl-brassinin; N-[2-(indol-3-yl)ethyl]-S-benzyl-dithiocarbamate; N-[2-(indol-3-yl)ethyl]-S[(naphth-2-yl)methyl]-dithiocarbamate; N-[2-(indol-3-yl)ethyl]-S-[(pyrid-3-yl)methyl]-dithiocarbamate; and N-[2-(indol-3-yl)ethyl]-S-[(pyrid-4-yl)methyl]-dithiocarbamate.

4. The compound of claim 3, wherein said compound is selected from the group consisting of N-[2-(benzo[b]thiophen-3-yl)ethyl]-S-methyl-dithiocarbamate;
N-[3-(Indol-3-yl)propyl]-S-methyl-dithiocarbamate; S-Allyl-brassinin; S-Benzyl-brassinin; N-[2-(indol-3-yl)ethyl]-S-benzyl-dithiocarbamate; N-[2-(indol-3-yl)ethyl]-S-[(naphth-2-yl)methyl]-dithiocarbamate; N-[2-(indol-3-yl)ethyl]-S-[(pyrid-3-yl)methyl]-dithiocarbamate; and N-[2-(indol-3-yl)ethyl]-S-[(pyrid-4-yl)methyl]-dithiocarbamate.

5. A composition comprising the compound of claim 1 and a pharmaceutically acceptable carrier medium.

6. The composition of claim 5 further comprising at least one signal transduction inhibitor (STI).

7. The pharmaceutical composition of claim 6, wherein at least one of said compounds is selected from the group consisting of N-[2-(Indol-3-yl)ethyl]-S-methyl-dithiocarbamate; N-[2-(benzo[b]thiophen-3-yl)ethyl]-S-methyl-dithiocarbamate; N-[3-(Indol-3-yl)propyl]-S-methyl-dithiocarbamate; S-Allyl-brassinin; S-Benzyl-brassinin; S-Hexyl-brassinin; N-[2-(indol 3-yl)ethyl]-S-benzyldithiocarbamate; N-[2-(indol-3-yl)ethyl]-S-[(naphth-2-yl)methyl]-dithiocarbamate; N-[2-(indol-3-yl)ethyl]-S-[(pyrid-3-yl)methyl]-dithiocarbamate; and N-[2-(indol-3-yl)ethyl]-S-[(pyrid-4-yl)methyl]-dithiocarbamate.

8. The composition of claim 5 further comprising at least one chemotherapeutic agent.

9. The composition of claim 8, wherein at least one of said compounds is selected from the group consisting of N-[2-(Indol-3-yl)ethyl]-S-methyl-dithiocarbamate; N-[2-(benzo[b]thiophen-3-yl)ethyl]-S-methyl-dithiocarbamate; N-[3-(Indol-3-yl)propyl]S-methyl-dithiocarbamate; S-Allyl-brassinin; S-Benzyl-brassinin; S-Hexyl-brassinin; N-[2-(indol-3-yl)ethyl]-S-benzyl dithiocarbamate; N-[2-(indol-3-yl)ethyl]-S-[(naphth-2-yl)methyl]-dithiocarbamate; N-[2-(indol-3-yl)ethyl]-S[(pyrid-3-yl)methyl]-dithiocarbamate; and N-[2-(indol-3-yl)ethyl]-S-[(pyrid-4-yl)methyl]-dithiocarbamate.

10. The composition of claim 8, wherein said at least one chemotherapeutic agent is selected from the group consisting of paclitaxel, cisplatin, docetaxol, carboplatin, vincristine, vinblastine, methotrexate, cyclophosphamide, CPT-11, 5 fluorouracil (5-FU), gemcitabine, estramustine, carmustine, adriamycin (doxorubicin), etoposide, arsenic trioxide, irinotecan, and epothilone derivatives.

11. The compound of claim 1, wherein n is 1 to 3.

12. The compound of claim 1, wherein said compound is N-[2-(indol-3-yl)ethyl]-S[(naphth-2-yl)methyl]-dithiocarbamate.

* * * * *